(12) United States Patent
Kalmeta

(10) Patent No.: US 11,745,026 B2
(45) Date of Patent: *Sep. 5, 2023

(54) LASER ASSISTED WOUND HEALING PROTOCOL AND SYSTEM

(71) Applicant: THE BIOREGENTECH INSTITUTE, INC., Irvine, CA (US)

(72) Inventor: Margaret V. Kalmeta, Irvine, CA (US)

(73) Assignee: THE BIOREGENTECH INSTITUTE, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/811,651

(22) Filed: Nov. 13, 2017

(65) Prior Publication Data

US 2018/0154172 A1    Jun. 7, 2018

Related U.S. Application Data

(63) Continuation-in-part of application No. 15/348,793, filed on Nov. 10, 2016, now Pat. No. 11,389,663,
(Continued)

(51) Int. Cl.
*A61N 5/06* (2006.01)
*A61C 1/00* (2006.01)
(Continued)

(52) U.S. Cl.
CPC .......... *A61N 5/0603* (2013.01); *A61C 1/0046* (2013.01); *A61C 19/043* (2013.01);
(Continued)

(58) Field of Classification Search
CPC ................ A61N 5/0603; A61N 5/0616; A61N 2005/0662; A61N 5/0624;
(Continued)

(56) References Cited

U.S. PATENT DOCUMENTS 3,950,529 A    4/1976    Fischer et al.
5,292,362 A    3/1994    Bass et al.
(Continued)

FOREIGN PATENT DOCUMENTS

EP       1224924      7/2002
TW       469045    *  1/2014
(Continued)

OTHER PUBLICATIONS

Koort et al., Laser, Industry Report "A combined device for optimal soft tissue applications in laser dentistry", 4, Jan. 2013, pp. 24-29. (Year: 2013).*

(Continued)

*Primary Examiner* — Lezah Roberts
(74) *Attorney, Agent, or Firm* — PILLSBURY WINTHROP SHAW PITTMAN LLP

(57) ABSTRACT

The present invention provides for devices and methods of treating wounds, including general wounds, gum disease and gingival tissues post scaling/root planning, using a diode laser which generates a beam of light having a wavelength in the visible portion of the electromagnetic spectrum (400 nm-700 nm). Further disclosed are devices and methods capable of stimulating tissue regeneration at the site of a wound.

9 Claims, 40 Drawing Sheets

Related U.S. Application Data which is a continuation-in-part of application No. 14/937,858, filed on Nov. 10, 2015, which is a continuation-in-part of application No. 13/864,226, filed on Apr. 16, 2013, now Pat. No. 9,180,319, which is a continuation-in-part of application No. 13/078,757, filed on Apr. 4, 2011, now abandoned.

(51) Int. Cl.
  *A61K 33/42* (2006.01)
  *A61K 38/39* (2006.01)
  *A61C 19/04* (2006.01)
  *A61N 5/067* (2006.01)

(52) U.S. Cl.
  CPC .............. *A61K 33/42* (2013.01); *A61K 38/39* (2013.01); *A61N 5/067* (2021.08); *A61N 5/0616* (2013.01); *A61N 5/0624* (2013.01); *A61N 2005/063* (2013.01); *A61N 2005/0606* (2013.01); *A61N 2005/0644* (2013.01); *A61N 2005/0651* (2013.01); *A61N 2005/0662* (2013.01); *A61N 2005/0663* (2013.01)

(58) Field of Classification Search
  CPC .... A61N 2005/0651; A61N 2005/0663; A61N 2005/0606; A61N 2005/063; A61N 2005/0644; A61N 5/067; A61C 1/0046; A61C 19/043; A61K 33/42; A61K 38/39
  See application file for complete search history.

(56) References Cited

U.S. PATENT DOCUMENTS

| | | | |
|---|---|---|---|
| 5,391,550 A | 2/1995 | Carniglia et al. | |
| 5,464,436 A | 11/1995 | Smith | |
| 5,616,313 A | 4/1997 | Williams et al. | |
| 5,642,997 A | 7/1997 | Gregg, II et al. | |
| 6,221,068 B1 * | 4/2001 | Fried .................... | A61B 18/20 128/898 |
| 6,878,145 B2 * | 4/2005 | Brugger ............... | A61B 18/201 606/18 |
| 7,107,996 B2 | 9/2006 | Ganz et al. | |
| 7,621,745 B2 | 11/2009 | Bornstein | |
| 2003/0158111 A1 | 8/2003 | Bar-Or | |
| 2004/0009598 A1 | 1/2004 | Hench et al. | |
| 2004/0199227 A1 | 10/2004 | Altshuler et al. | |
| 2004/0259053 A1 | 12/2004 | Bekov et al. | |
| 2006/0210494 A1 | 9/2006 | Rabiei et al. | |
| 2006/0241595 A1 | 10/2006 | Kurtz | |
| 2007/0021807 A1 | 1/2007 | Kurtz | |
| 2008/0033514 A1 | 2/2008 | Kurtz | |
| 2008/0033515 A1 | 2/2008 | Kurtz | |
| 2008/0060148 A1 | 3/2008 | Pinyayev | |
| 2009/0087816 A1 | 4/2009 | Bornstein | |
| 2010/0029549 A1 | 2/2010 | Chaput et al. | |
| 2010/0076526 A1 | 3/2010 | Krespi et al. | |
| 2010/0098746 A1 | 4/2010 | King | |
| 2012/0251972 A1 | 10/2012 | Kalmeta | |
| 2012/0330288 A1 * | 12/2012 | Clementi ............... | A61B 18/20 606/9 |
| 2013/0267943 A1 | 10/2013 | Hancock | |
| 2014/0074090 A1 * | 3/2014 | Lam ..................... | A61B 18/042 606/49 |
| 2014/0113243 A1 | 4/2014 | Boutoussov et al. | |
| 2014/0141389 A1 | 5/2014 | Kalmeta | |
| 2015/0164618 A1 | 6/2015 | Heacock et al. | |
| 2015/0283287 A1 | 10/2015 | Agarwal et al. | |
| 2016/0158284 A1 | 9/2016 | Kalmeta | |
| 2017/0120070 A1 | 5/2017 | Kalmeta | |

FOREIGN PATENT DOCUMENTS

| | | | |
|---|---|---|---|
| WO | 2007/027620 A1 | | 3/2007 |
| WO | WO 2008/068749 | * | 6/2008 |
| WO | 2011/096003 A1 | | 8/2011 |
| WO | 2012130771 | | 10/2012 |
| WO | 2017083579 A1 | | 5/2017 |

OTHER PUBLICATIONS

European Patent Office, Extended European Search Report issued in EP Patent Application No. 17870468.0, dated Oct. 28, 2020, pp. 1-14.

IP Australia, Examination Report issued in AU Patent Application No. 2020200444, dated May 24, 2021, pp. 1-6.

Schwarz et al., "The impact of laser application on periodontal and peri-implant wound healing", Periodontol 2000, Aug. 20, 2009, pp. 79-108, vol. 51.

Amorim et al., "Clinical study of the gingiva healing after gingivectomy and low-level laser therapy", Photomed Laser Surg., 2006, pp. 588-594, vol. 24(5).

Rodrigues et al., "Modulation of phosphate/pyrophosphate metabolism to regenerate the periodontium: a novel in vivo approach", J Periodontol, Dec. 2011, pp. 1757-1766, vol. 82(12).

Koort et al., "A combined device for optimal soft tissue applications in laster dentistry", Laser Industry Report, Jan. 2013, pp. 24-29.

United States Patent and Trademark Office, Non-Final Office Action issued in U.S. Appl. No. 15/811,651, dated Jul. 15, 2021.

United States Patent and Trademark Office, Final Office Action issued in U.S. Appl. No. 16/349,222, dated Feb. 18, 2022, p. 9.

United States Patent and Trademark Office, Official Action issued in U.S. Appl. No. 14/937,858, dated Jul. 11, 2022, pp. 1-6.

Asai et al. "Maxillary Sinus Augmentation Model in Rabbits" Effect of Occluded Nasal Ostium on New Bone Formation. (2002) Clin. Oral Impl. Res. 13:405-409.

Goldstep—www..oralhealthjournal com—Diode Lasers for Periodontal Treatment: The story so far. Publication Dec. 2009, p. 44-46.

Ozcelik—http://www.ncbi.nlm.nih.gov/pubmed/148081859—Enamel matrix derivative and low-level laser therapy in the treatment of intra-bony defects: a randomized placebo-controlled clinical trial—J. Clin. Periodontol. Feb. 2008. 35(2):56-147. Epub Dec. 13, 2007.

* cited by examiner

Fig. 8    4-15-10
Fig. 9    2-22-11

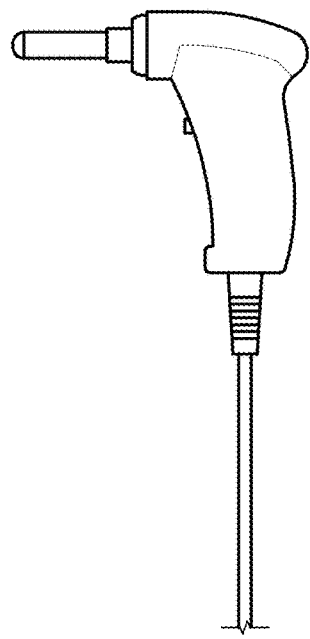
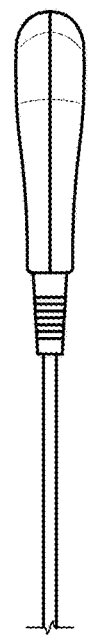
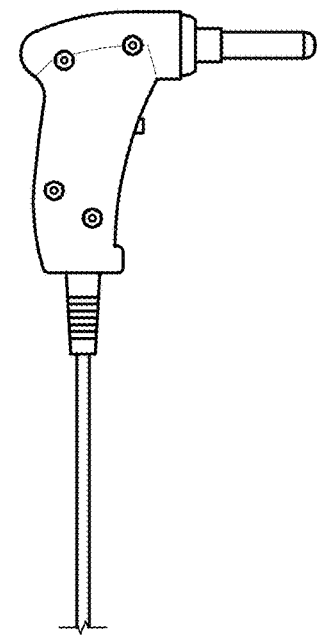
FIG. 17A     FIG. 17B     FIG. 17C
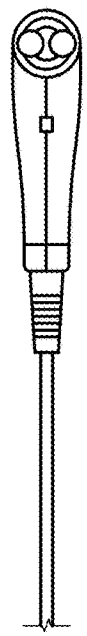
FIG. 17E
FIG. 17F
FIG. 17D

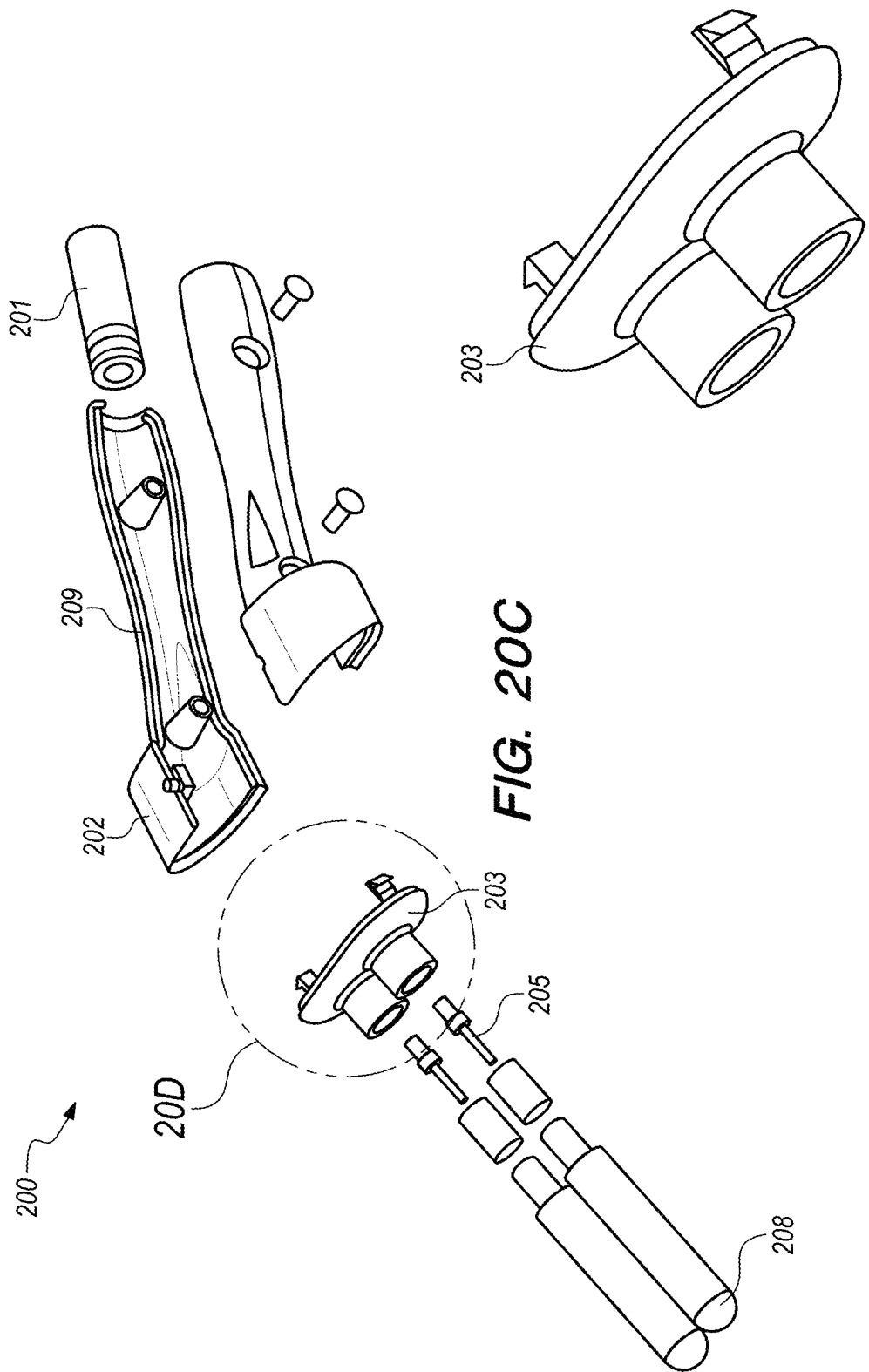

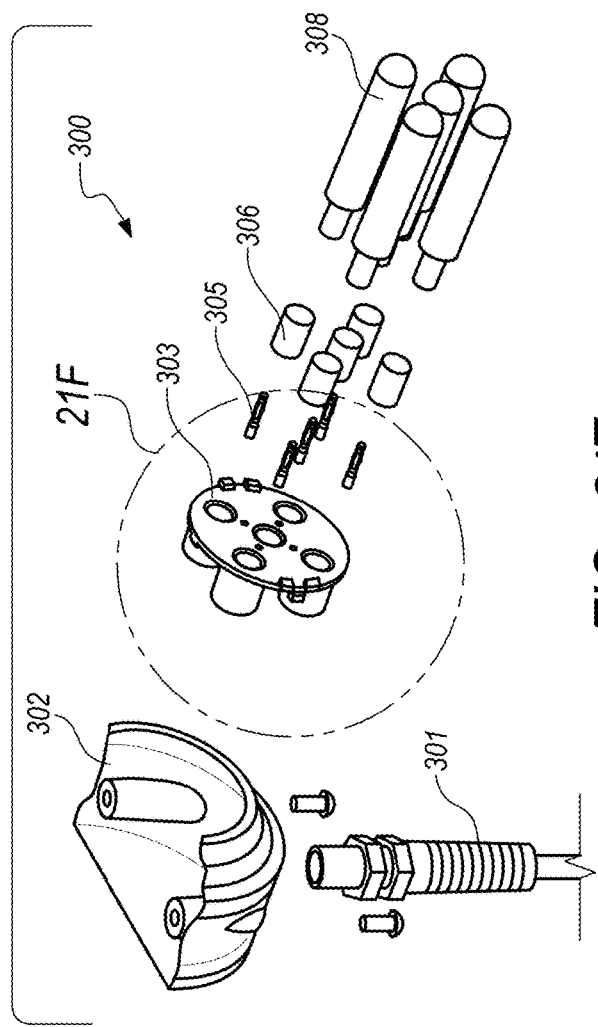
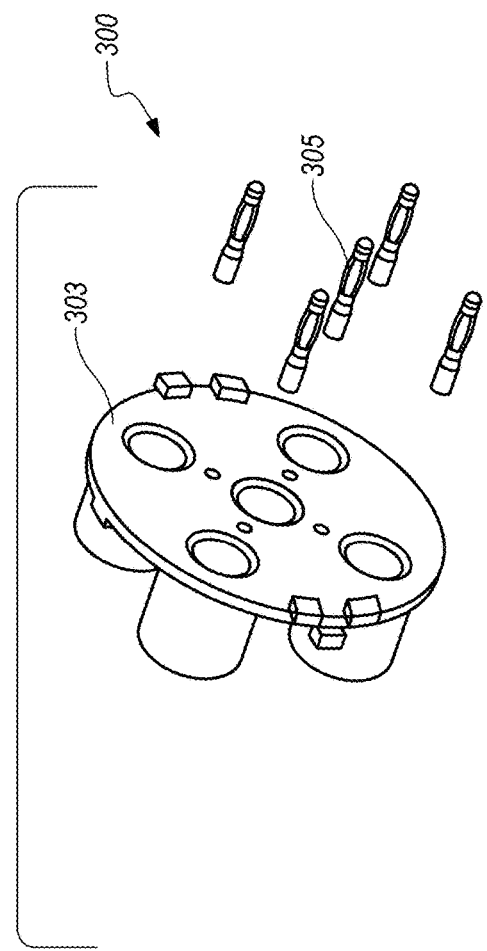
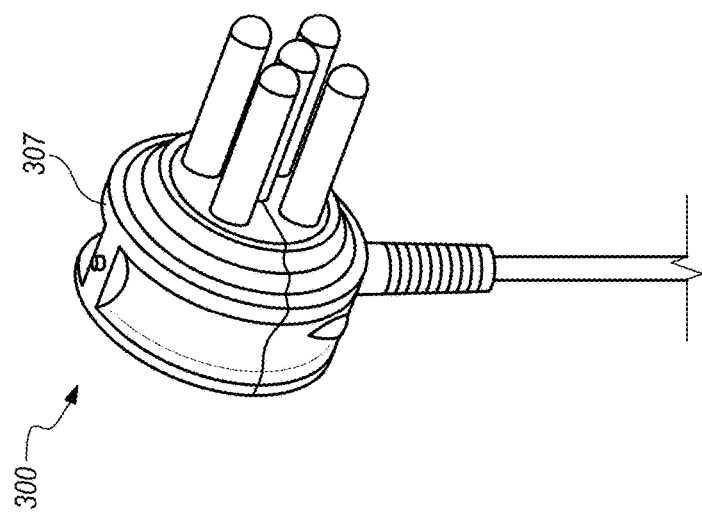

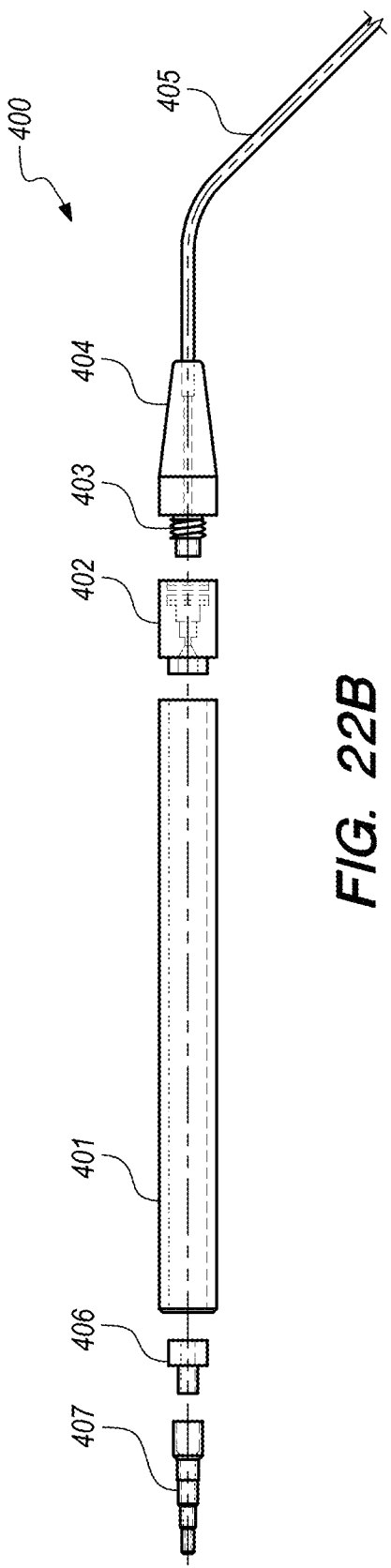
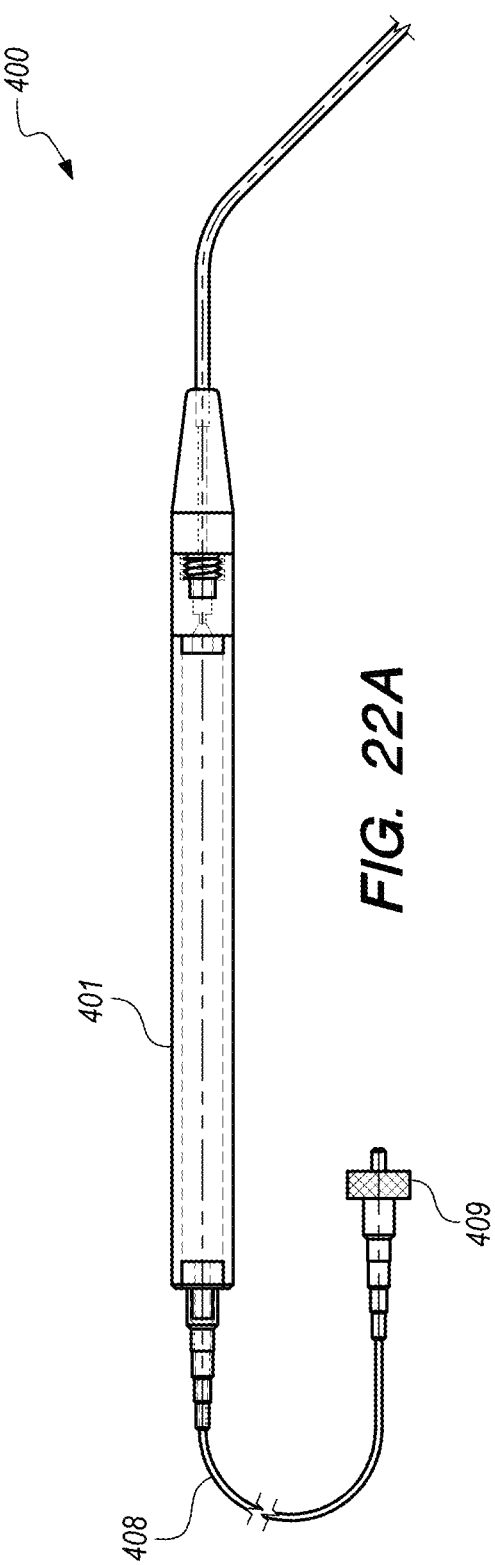

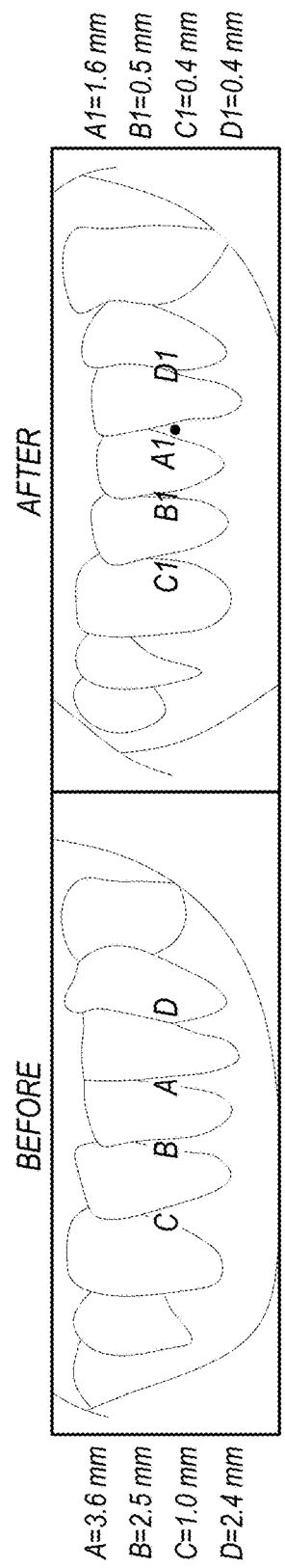
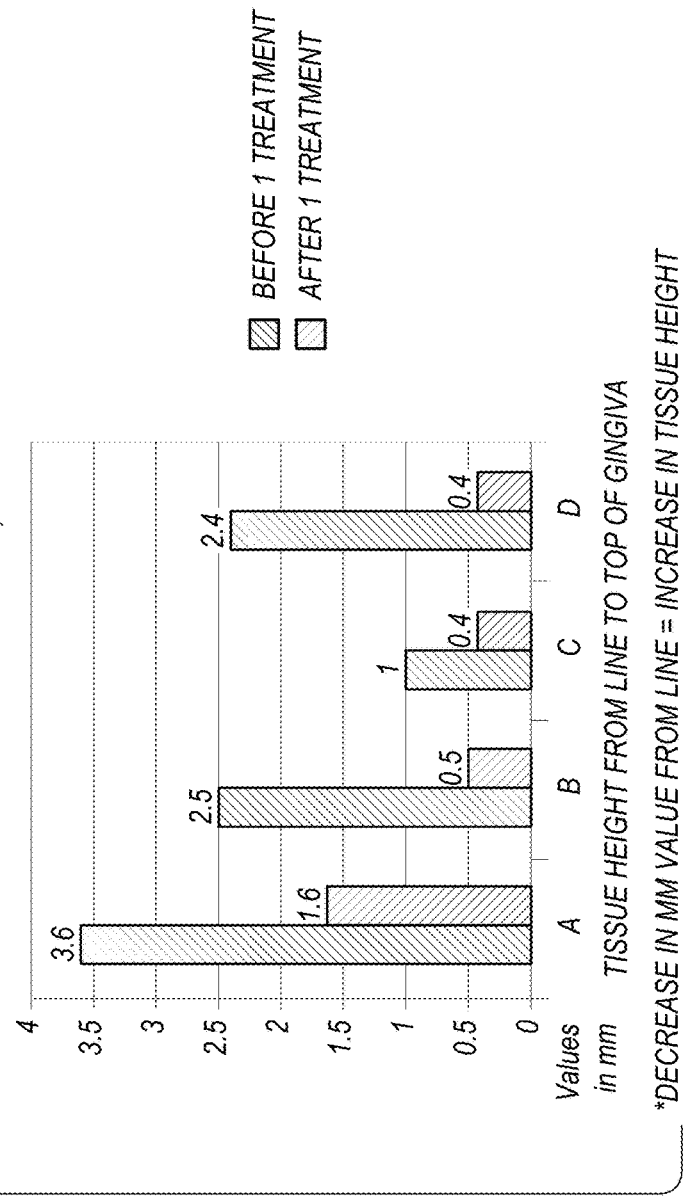
FIG. 26A
FIG. 26B
FIG. 26C

LASER ASSISTED WOUND HEALING PROTOCOL AND SYSTEM

CROSS REFERENCES

This application is a Continuation-In-Part patent application claiming the benefit of priority under 35 U.S.C. 120 from U.S. patent application Ser. No. 15/348,793 filed Nov. 10, 2016, which claims the benefit of priority from U.S. patent application Ser. No. 14/937,858 filed Nov. 10, 2015 which claims the benefit of priority from U.S. patent application Ser. No. 13/864,226 filed Apr. 16, 2013, now issued U.S. Pat. No. 9,180,319, which claims the benefit of priority from U.S. patent application Ser. No. 13/078,757 filed Apr. 4, 2011, now abandoned, the entire contents of which are herein incorporated by reference.

FIELD OF THE INVENTION

The present invention relates generally to a method of treating gum diseases using a diode laser which produces a beam of light having a wavelength in the visible portion of the electromagnetic spectrum (400 nm-700 nm). Optionally, the laser light utilizes green wavelength range (520-570 nm) at a laser power 0.001 W to 5 W to treat wounds. It is also contemplated that described is a method of treating diseased soft or hard tissue using a diode laser. Optionally, the laser light utilizes the IR wavelength range (700 nm-1400 nm) at a laser power of 0.001 W to 5 W to treat wounds. Optionally, an LED light utilizes the IR wavelength range to treat wounds.

BACKGROUND OF THE INVENTION

Laser Assisted Periodontium and Osseous Regeneration (LAPOR) is a protocol which is laser assisted with the use of a substrate such as but not limited the LAPOR periodontal solution, the LAPOR periodontal gel and the LAPOR substrate and thus causes an increase in cell attachment of epithelial cells, gingival fibroblasts, PDL fibroblasts and adhesion of osteogenic cells. Enhanced cell migration and proliferation appears to lead to accelerated wound fill rates in vitro using PDL fibroblasts, gingival fibroblasts and osteoblast-like cells.

A substrate such as the LAPOR periodontal solution, the LAPOR periodontal gel and the LAPOR substrate, used in the LAPOR protocol, stimulates total protein synthesis and the synthesis of specific extracellular matrix molecules. Studies that evaluate the bone remodeling regulation system indicate that proteins influence this regulation system, thus indicating an indirect involvement in the bone remodeling process. When used in conjunction with a specially formulated periodontal and wound healing substrate or combination of substrates, and LAPOR gel root conditioner in certain cases, LAPOR has shown to stimulate total tissue and bone synthesis, increase gingival attachment, gingival height, bone density, bone height thereby showing accelerated wound fill rates in vivo.

The laser or LED used produces a beam of light having a wavelength in the visible portion of the electromagnetic spectrum (400 nm-700 nm). Optionally, a beam of light having a wavelength in the green wavelength range (520-570 nm) at a laser power of 0.5 to 1.2 W is used in the LAPOR protocol. It has been shown by the LAPOR protocol to biostimulate the healing and regenerative processes of the periodontium, including the biostimulation of new bone and its supporting elements. The diode laser used in the LAPOR protocol, biostimulates the healing response of the periodontium, and biostimulates the soft or hard tissue regeneration of the periodontium, and prevents long junctional epithelium from migrating downwards into the sulcus (a biomechanical aspect of tissue healing), thereby preserving the tissue height. A diode laser used in the LAPOR protocol helps a substrate such as but not limited to compounds and proteins to stimulate total protein synthesis and the synthesis of extracellular matrix molecules.

Alternatively, the LAPOR protocol may use a beam of light having a wavelength in the green wavelength range (520-570 nm), red wavelength range (620-750 nm), or yellow wavelength range (570-590 nm) having an alternative wattage of 0.001 W to 5 W, preferably 0.002 W to 4 W, more preferably 0.003 W to 4 W, and most preferably 0.005 W to 2 W. The diode laser used helps the substrate(s) stimulate total tissue and bone synthesis by biostimulating the healing response via soft/hard tissue regeneration of a wound and soft/hard tissue regeneration of the wound's supporting elements.

It is further contemplated that the invention may be used to treat soft and/or hard tissue damage in wounds, i.e. Laser Assisted Tissue and Osseous Regeneration (LATOR) using a LATOR solution, and/or LATOR gel and/or a LATOR substrate or a combination of substrates to enhance cell migration and proliferation leading to accelerated wound fill rates. The protocol is used in conjunction with a choice or any combination of six specially formulated tissue and wound healing substrates and a gel conditioner in certain cases to stimulate total tissue and bone synthesis, increase tissue attachment, tissue height, bone density and bone height thereby showing accelerated would fill rates, showing a mechanism of action as in the LAPOR protocol.

SUMMARY OF THE INVENTION

In an exemplary embodiment of the present invention, there is disclosed a method of treating wounds, including general wounds, gum disease and gingival tissues post scaling/root planning, using a diode laser which generates a beam of light having a wavelength in the visible portion of the electromagnetic spectrum (400 nm-700 nm). Optionally, a beam of light having a wavelength in the green range (520-570 nm) at a laser power of 0.5 to 1.2 watts is used to decontaminate the wound or gum tissue and to biostimulate healing while regenerating the wound or periodontium (including cementum of the root surface and/or tissues surrounding an implant), thus preventing long junctional epithelium from migrating downwards into the sulcus and thereby preserving the tissue height. Alternatively, a beam of light having a wavelength in the green wavelength range (520-570 nm), red wavelength range (620-750 nm), or yellow wavelength range (570-590 nm) having an alternative wattage of 0.001 W to 5 W may be used to biostimulate healing and regenerate the wound site, its tissue and bone. In a preferred embodiment, the wattage is in the range of 0.002 W to 4 W, more preferred in the range of 0.003 to 3 W, and most preferred in the range of 0.005 W to 2 W. A laser or LED also biostimulates the healing and regenerative response induced by a substrate, i.e. the LAPOR periodontal and wound healing solution, the LAPOR periodontal gel and the LAPOR periodontal and wound healing substrates, the method comprising: 1) placing the laser inside the sulcus; 2) penetrating the entire sulcus by moving the laser light intermittently vertically and horizontally throughout the sulcus; and 3) placing the substrate in the sulcus prior to blood clot formation. In a preferred embodiment, the LATOR protocol may use a laser per the above parameters to treat general wound sites. Optionally, the laser light utilizes the IR wavelength range (700 nm-1400 nm) at a laser power or average power of 0.001 W to 5 W to treat wounds.

In an alternative embodiment, the LAPOR or LATOR protocol may use an LED light to biostimulate healing and to regenerate periodontium or general wound tissue. The LED light is used at 10 W or, preferably, 9 W or lower on wounds to assist in new cell organization and hence tissue regeneration. Optionally, an LED light utilizes the IR wavelength range to treat wounds. Optionally, the laser light utilizes the IR wavelength range (700 nm-1400 nm) at a laser power of 0.001 W to 5 W to treat wounds.

In an alternative embodiment, the LAPOR and LATOR protocols may use a radiofrequency (RF) wave to decrease pain or decontaminate the gum tissue and biostimulate healing while regenerating the periodontium and wound. The RF beam is used at 10 W or, preferably, 9 W or lower on wounds to assist in new cell organization and hence soft and/or hard tissue regeneration. A carrier wave (sine wave) transports a non-sinusoidal waveform or waveforms to the treatment location. The carrier wave frequency may be in the range of 0.1 MHz to 20 MHz while the non-sinusoidal waveform may be in the range of 0.5 to 40 KHz or alternatively 0.5-24 GHz. In a preferred embodiment, the carrier wave frequency is in the range of 0.2 MHz to 10 MHz, preferably 0.3 MHz to 5 MHz. Optionally the 0.001 W to 10 W or 9 W range, preferably a 0.001 W to 3 W range, is utilized in the hertz range of 40 Hz to 24 GHz. In a further alternative embodiment, the RF wave is a single sine wave. In a further alternative embodiment, the RF wave is more than one sine wave wherein the more than one demonstrates a harmonics pattern. In a preferred embodiment, the LATOR protocol may use an RF wave per the above parameters to treat general wound sites. Optionally, the non-sinusoidal waveform/s may be in the range of the above parameters in the absence of a carrier wave.

In another embodiment of the present invention, there is disclosed a root/bone/cartilage gel conditioner comprised of EDTA 15%, calcium gluconate 20%, methylparaben, propylparaben, Ethanolamine as a buffering agent, carboxymethylcellulose, and green food coloring and sterile water.

In still another embodiment of the present invention, there is disclosed a first substrate comprised of: a combination of mono or disodium phosphate and sodium hydroxide in solution with a sodium content of 11 mg/100 g; 60% water; 9% Lysine; 9% Proline; 9% all other essential amino acids wherein the amino acids are chosen from the group consisting of Isoleucine, Leucine, Methionine, Phenylalanine, Threonine, Tryptophan, Valine, Histadine, Asparagine and Selenocysteine; 2% of all other non-essential amino acids wherein the amino acids are chosen from the group consisting of Alanine, Arginine, Aspartate, Cysteine, Glutamate, Glutamine, Glycine, Serine, Tyrosine and Pyrrolsine; 6.9% free bases wherein the free bases are chosen from the group consisting of adenosine, uridine, guanosine, iridin and cytidine; 2% phosphates wherein the phosphates are chosen from the group consisting of ADP, ATP and acetycholine; and 1% benzoic acid.

In still another embodiment of the present invention, there is disclosed a second substrate comprised of: tricalcium phosphate wherein the tricalcium phosphate is precipitated with calcium hydroxide/Claw oil; and hydroxyapatite crystals. Optionally, the second substrate is comprised of tricalcium phosphate wherein the tricalcium phosphate is prepared with hydroxyapatite crystals, wherein the second substrate is comprised of dense or porous tricalcium phosphate comprising of one size or variety of sizes of crystals: 4-50 μm, 50-150 μm, 100-300 μm, 500-1000 μm, 1-3 mm, and 3-6 mm.

In yet another embodiment of the present invention, there is disclosed a third substrate comprised of: 5.1% hyaluronic acid; 8% fatty acids wherein the fatty acids are chosen from the group consisting of Linoleic acid (LA), alpha-linolenic acid (ALA), 4.4% sugars wherein the sugars are chosen from the group consisting of mannose, galactose, N-acetyllactosamine, N-acetylglucosamine, N-acetylneuraminic acid, fucose (L configuration minus a carboxyl group at the 6 position), and xylose; 2.2% mixture of glucose and fucose (L configuration minus a carboxyl group at the 6 position); 3% lipids wherein the lipids are chosen from the group consisting of vitamin A, vitamin D2, D3, vitamin E, vitamin K1, K2, vitamin B12 (methylcobalamin, hydroxocobalamin), cholesterol, and diaglycerol; 2.7% vitamins wherein the vitamins are chosen from the group consisting of vitamin B1, vitamin B2, vitamin B3, vitamin B5, vitamin B6, vitamin B7, vitamin B9, vitamin C and pantothenic acid; 4.5% electrolyte sources: wherein the electrolyte sources are chosen from the group consisting of Calcium Chloride, Choline Chloride, Magnesium Sulfate, Potassium Chloride, Potassium Phosphate (monobasic), Sodium Bicarbonate, Sodium Chloride, and Sodium Iodide; 6% metals wherein the metals are chosen from the group consisting of Ag nanoparticles and Au nanoparticles; 3.9% ionic metals wherein the ionic metals are chosen from the group consisting of copper, zinc, selenium, iron, manganese, cobalt, chromium, boron, and molybdenum; and 4% other ionic metals wherein the other ionic metals are chosen from the group consisting of boron, silicon, nickel and vanadium.

In another embodiment of the present invention, there is disclosed a fourth substrate comprised of carbomer, potassium chloride, chloride, sodium, potassium, manganese, calcium tri-phosphate, sulfate, carbonate, snail serum, snail secretion filtrate, HA, Au, Ag, Cu, Fe, Pt, collagen, glyceine HCl and fucose.

In another embodiment of the present invention, there is disclosed as fifth substrate comprised of a dense or porous tricalcium phosphate in a variety of crystal sizes, and/or collagen limed and/or collagen unlimed.

In another embodiment of the present invention, there is disclosed a sixth substrate comprised of a dense or porous tricalcium phosphate in a variety of crystal sizes, and/or collagen limed and/or collagen unlimed and/or HCl and/or NaCl, and/or nanoparticles wherein the nanoparticles are chosen from the group consisting of copper, Au, Ag, iron, $Fe_3O_4$, and platinum or any combination thereof and/or compounds wherein the compounds are chosen from the group consisting of $CuCl_3$, $CuCl_2$, CuCl, $FeCl_3$, $FeCl_2$, AuCl, $AuCl_2$, $AuCl_3$, AgCl, $AgCl_2$ or any combination thereof, and/or Hyaluronic Acid and/or dense or porous hydroxyapatite in a variety of crystal sizes.

The more important features of the invention have thus been outlined in order that the more detailed description that follows may be better understood and in order that the present contribution to the art may better be appreciated. Additional features of the invention will be described hereinafter and will form the subject matter of the claims that follow.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

The foregoing has outlined, rather broadly, the preferred feature of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention and that such other structures do not depart from the spirit and scope of the invention in its broadest form.

BRIEF DESCRIPTION OF THE DRAWINGS

Other aspects, features, and advantages of the present invention will become more fully apparent from the following detailed description, the appended claim, and the accompanying drawings in which similar elements are given similar reference numerals.

FIG. 8 shows an X-Ray view of the upper teeth before treatment with a diode laser after treatment with a substrate.

FIG. 9 shows an X-ray view of the upper teeth of FIG. 8 after treatment with a diode laser after treatment with a substrate.

FIG. 17a-17f show various views of a first embodiment of a diode laser with RF of the present invention. (a) shows a right side view. (b) shows a back side view. (c) shows a left side view. (d) shows a front side view. (e) shows a top view. (f) shows a bottom view.

FIG. 20a-20d shows views of the RF device with and without diode laser of FIG. 19. (a) shows an exploded view of RF device with laser. (b) shows a close-up of the handpiece with laser relative to housing. (c) shows an exploded view of RF device without laser. (d) shows detailed view of housing for RF device without laser.

FIG. 21a-21f show various views of a third embodiment of the RF device of the present invention, with and without the laser. (a) shows a side perspective view. (b) shows an exploded view of the RF device with laser. (c) shows a close-up view of the laser relative to the sub-housing. (d) shows a side perspective view. (e) shows an exploded view of the RF device without laser. (f) shows a detailed view of the sub-housing within the RF device without laser.

FIG. 22a-22h shows fiber optic handpiece and tip embodiments of the present invention, along with the power device and battery embodiments for the handpieces. (a) shows an assembled view. (b) shows an exploded view. (c) shows a flat tip. (d) shows a glass dispersion tip. (e) shows an assembled view of the power device. (f) shows an exploded view of the power device. (g) shows an assembled view of the battery pack. (h) shows an exploded view of the battery pack.

FIG. 26a-26c show gingival wound healing and tissue regeneration measurements before and after treatment. (a) shows wounds before treatment. (b) shows tissue regeneration after treatment. (c) shows tissue height measurements before and after treatment.

DETAILED DESCRIPTION OF THE INVENTION

Definitions

Figure 1:
FIG. 1 shows an X-Ray view of a patient's teeth before treatment with a diode laser before a substrate has been applied.
Figure 2:
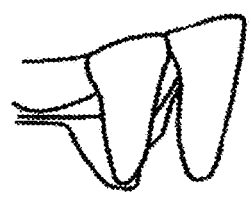
FIG. 2-7 show X-Ray views of the lower teeth of FIG. 1 after treatment with a diode laser after treatment with a substrate.
Figure 3:
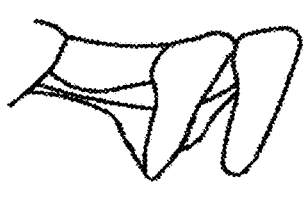
Figure 4:
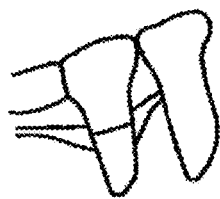
Figure 5:
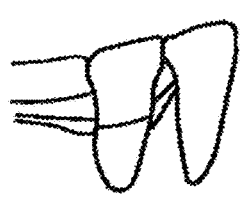
Figure 6:
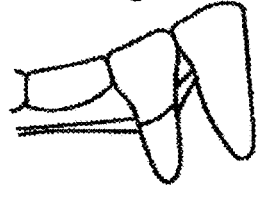
Figure 7:
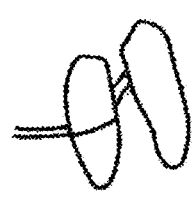

As used herein, the term "gum disease" means periodontal disease which can lead to tooth loss and/or other health problems. Examples of periodontal disease include gingivitis, aggressive periodontitis, chronic periodontitis, periodontitis as a manifestation of systemic diseases, and necrotizing periodontal disease.

As used herein, the term "tissue disease" means soft or hard tissue disease of acute or chronic nature which can lead to other health problems such as amputation of limbs.

As used herein, the term "patient" means any individual suffering from a disease of the gums or tissue and in need of treatment for said gum or tissue disease.

As used herein, the term "locus" means an exact point of measurement within the sulcus or the immediate surrounding area.

As used herein, the term "substrate mixture" means the mixture of the first substrate and/or the second substrate and/or the third substrate and/or the fourth substrate and/or the fifth substrate and/or sixth substrate disclosed herein for treatment of gum disease and/or tissue disease and/or wounds.

As used herein, the term "substrate" means any stand alone substrate of the substrates disclosed herein for treatment of gum disease and/or tissue disease and/or wounds.

As used herein, the term "bone regeneration" means increasing the density of calcium at specific loci in or around the sulcus or the immediate surrounding area.

As used herein, the term "calcium density" means the measurement of calcium mass around a given loci.

As used herein the term "wound" means any area that has lost any original tissue or bone or any other structure not named that lost a healthy non-wounded, undamaged and unaged form.

As used herein, the terms "power" and "average power" are considered synonymous, with "power" referring to continuous power applied to lasers, LEDs or RF devices while "average power" refers to pulsed power applied to lasers, LEDs or RF devices of the present invention.

As used herein, the terms "laser" or "LED" or "RF" mean types of energy and may be used with or without substrate.

The LAPOR protocol can be used in the treatment of gum disease and wounds by combining the most effective methods of treatment with the use of a special laser. Approximately 66% of the United States population has some form of gum disease. But many avoid seeking treatment because of the discomfort that often results from gum surgery. LAPOR provides a new choice. The LAPOR protocol is a treatment that is more effective than traditional periodontal surgery, and it is much more beneficial to the patient both in the short and long term. The LATOR protocol can similarly be used for treatment of soft or hard tissue disease and wounds.

The LAPOR protocol takes only about an hour and only two short follow-up visits. Patients enjoy no downtime with recovery taking only 24 hours. This makes immediate return to work both possible and comfortable.

After having the LAPOR protocol performed, no resulting gum recession occurs is zero when compared to that which most often follows normal periodontal surgery. This, combined with new cementum formation on the roots, bone formation in previous defects or around failing implants, periodontal ligament formation. After having the LATOR protocol performed in a chronic wound, no resulting subsequent wound fibrosis is found compared to that which most often follows normal treatment, new soft and/or hard tissue formation occurs multi directionally and the wound closes without grafting.

The LAPOR and LATOR protocols of the present invention can be used to heal wound sites by combining or using separately the most effective methods of treatment with the laser, LED, radiofrequency energy and substrates. In a preferred embodiment, the RF energy waves may be up to 10 W, with most preferably being only as high as 9 W. The carrier wave frequency may be in the range of 0.1 MHz to 20 MHz while the non-sinusoidal waveform/s may be in the range of 0.5 to 40 KHz or from 0.5 to 24 GHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one square wave wherein the more than one may demonstrate a pattern. In a further alternative embodiment, the RF wave is more than one sine wave wherein the more than one demonstrates a harmonics pattern.

The special type of laser used in the LAPOR protocol and the LATOR protocol is the diode, a semiconductor coherent light beam. The laser or LED light used has a wavelength in the visible portion of the electromagnetic spectrum, between 400 nm-700 nm wavelength. Optionally, the green range (520-570 nm) of the visible spectrum is utilized at a laser power or average power of 0.5 to 1.2 watts, which disinfects the site, leaving the gum tissue bacteria free, and biostimulates healing; in conjunction with treatment with a substrate, the laser biostimulates regeneration of the periodontium.

Traditional periodontal therapy removes tissue height of a tooth or implant to reduce the pocket depths. The LAPOR protocol is a regenerative procedure. The patient does not lose tissue volume. Tissue volume is increased and bone is regenerated. For general tissue disease, the laser biostimulates regeneration of tissue where traditional therapy removes tissue height to reduce the disease. Optionally, the laser light utilizes the IR wavelength range (700 nm-1400 nm) at a laser power or average power of 0.001 W to 5 W to treat wounds. Optionally, each LED light is used at 10 W or, preferably, 9 W or lower.

The use of the diode laser in conjunction with routine scaling and root planning is more effective than scaling and root planning alone. It enhances the speed and extent of the patients gingival healing and postoperative comfort. This is accomplished through laser bacterial reduction and biostimulation with a laser light having a wavelength in the visible portion of the electromagnetic spectrum, between 400 nm-700 nm wavelength. Optionally, the green range (520-570 nm) of the visible spectrum is utilized at a laser power or average power of 0.5 to 1.2 watts. Alternatively, the laser power wattage may be in the range of 0.001 W to 5 W, preferably 0.002 W to 4 W, more preferably 0.003 W to 3 W, and most preferably 0.005 W to 2 W.

Figure 10:
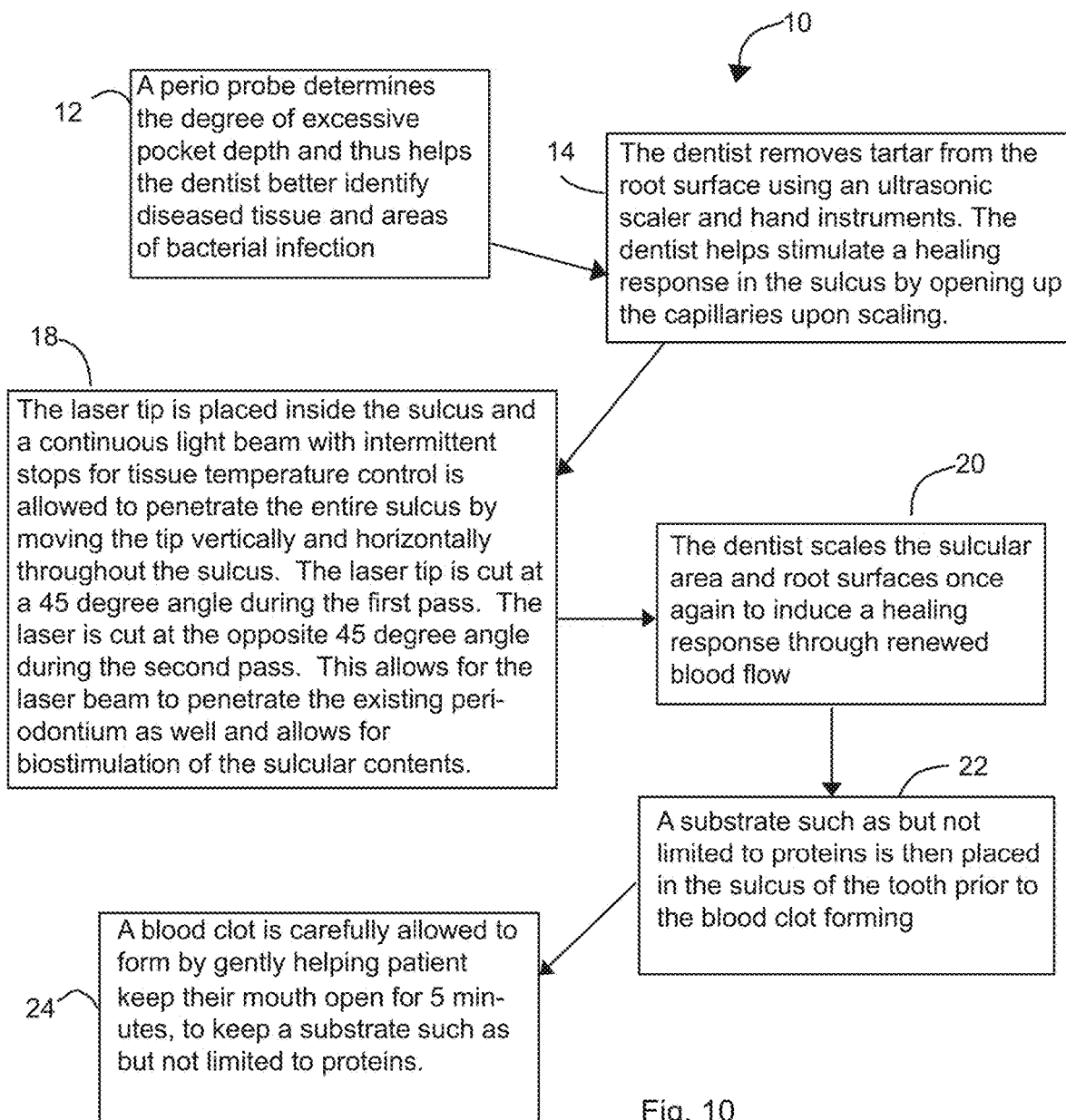
FIG. 10 shows a flow diagram of a method of using a diode laser to treat gum disease in accordance with the principles of the invention.

Referring to FIG. 10, there is disclosed a method 10 of using a diode laser which produces a beam of light, used intermittently, having a wavelength in the visible portion of the electromagnetic spectrum, between 400 nm-700 nm wavelength. Optionally, the green range (520-570 nm) of the visible spectrum is utilized at a laser power of 0.5 to 1.2 watts to treat gum disease. Starting at block 12, a period probe determines the degree of excessive pocket depth and thus helps the dentist better identify diseased soft and hard tissue and areas of bacterial infection. The dentist removes calculus from the root or implant surface using an ultrasonic scaler and hand instruments, block 14. This action by the dentist helps stimulate a healing response in the sulcus by opening the capillaries upon scaling. Going to block 18, the laser tip is placed inside the sulcus and a continuous light beam with intermittent stops for tissue temperature control is allowed to penetrate the entire sulcus by moving the tip vertically and horizontally throughout the sulcus. The laser tip is cut at a 45 degree angle during the first pass. The laser is cut at the opposite 45 degree angle during the second pass. This allows for the laser beam to penetrate the existing periodontium to decontaminate the tissue, as the heat of the targeted laser light kills the bacteria. This also allows for biostimulation of the sulcular contents. At block 20, the dentist scales the sulcular area and root/implant surfaces once again to induce a healing response through renewed blood flow. Going to block 22, at least one substrate, such as but not limited to matrix proteins, is then placed in the sulcus of the tooth prior to the blood clot forming and at block 24, a blood clot is carefully allowed to form by gently helping patient keep their mouth open for 5 minutes, to keep the substrate intact. Optionally, the laser light utilizes the IR wavelength range (700 nm-1400 nm) at a laser power of 0.001 W to 5 W to treat wounds.

Alternatively, the laser tip is a specially designed tip that disperses light energy throughout the wounded sulcus which allows the laser beam to penetrate the existing tissues to decontaminate the tissue, as the heat of the targeted laser light kills the bacteria and as a result block 20 may be eliminated going directly to block 22

The LAPOR protocol is much less invasive than traditional surgery and offers advantages and benefits over its counterpart. Recovery time is much faster because most, if not all, damage to healthy tissue is avoided through the use of more advanced technology. Because the LAPOR protocol leaves healthy tissue intact, the height of the gums themselves increases around the teeth and is better preserved. The LAPOR protocol prevents long junctional epithelium from migrating downwards into the sulcus, thus preserving the tissue height and allowing for the regeneration of the periodontium.

Figure 18A:
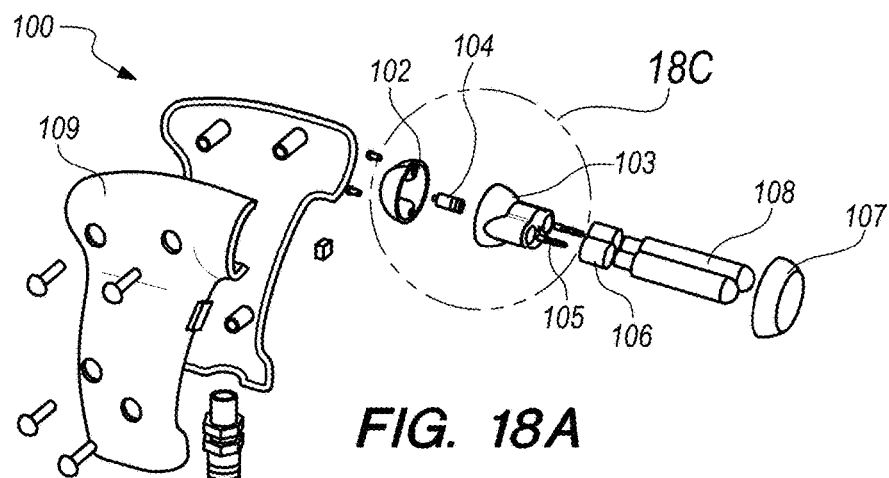
FIG. 18a-18c show an exploded view of the diode laser of FIG. 17. (a) shows an exploded view. (b) shows an assembled view. (c) shows a close-up of the laser housing.
Figure 18B:
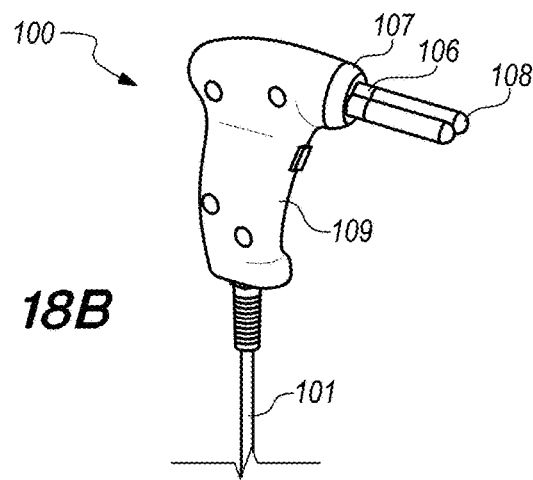
Figure 18C:
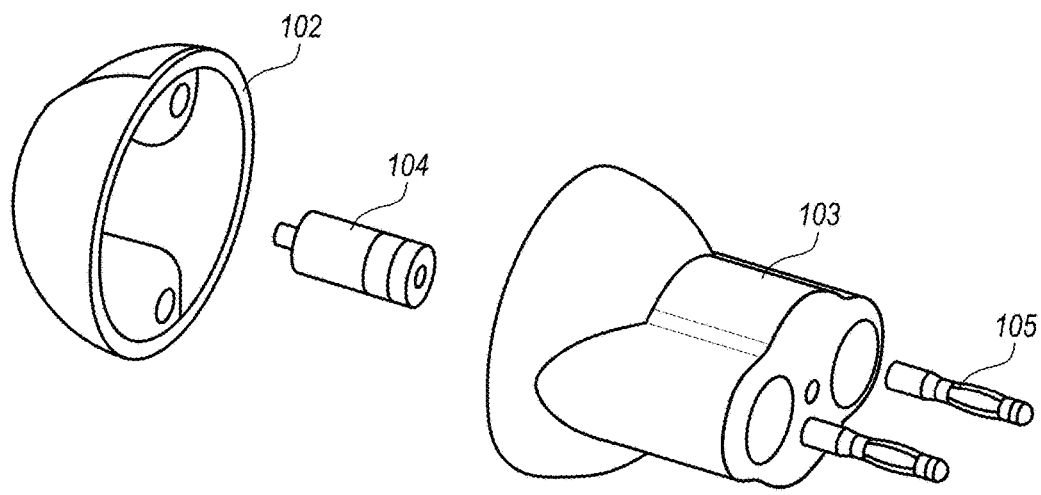
Figure 19A:
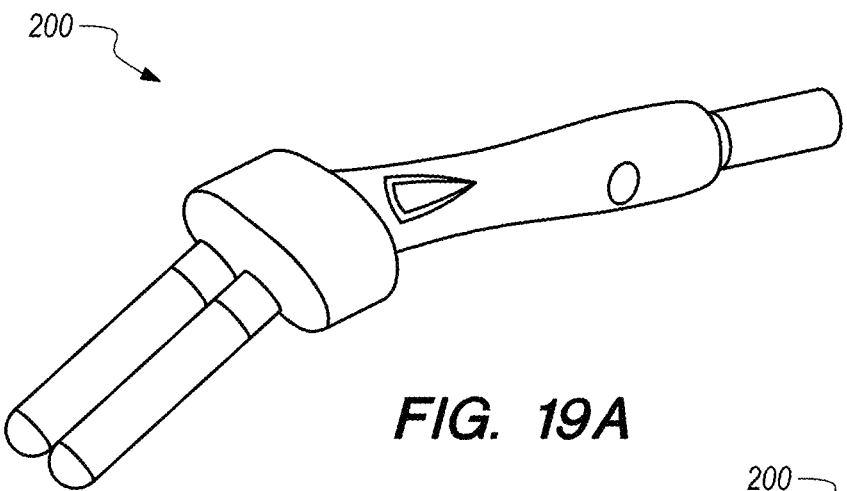
FIG. 19a-19g shows various views of a second embodiment of the RF device without diode laser of the present invention. (a) shows a top perspective view. (b) shows a back view. (c) shows a left side view. (d) shows a top view. (e) shows a front perspective view. (f) shows a right side view. (g) shows a bottom view.
Figure 19B:
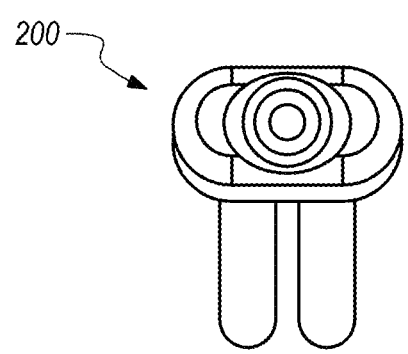
Figure 19C:
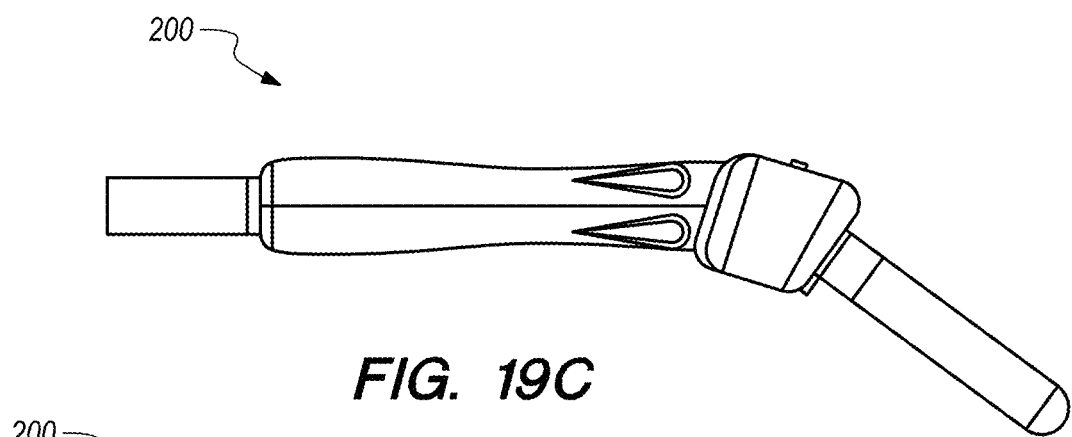
Figure 19D:
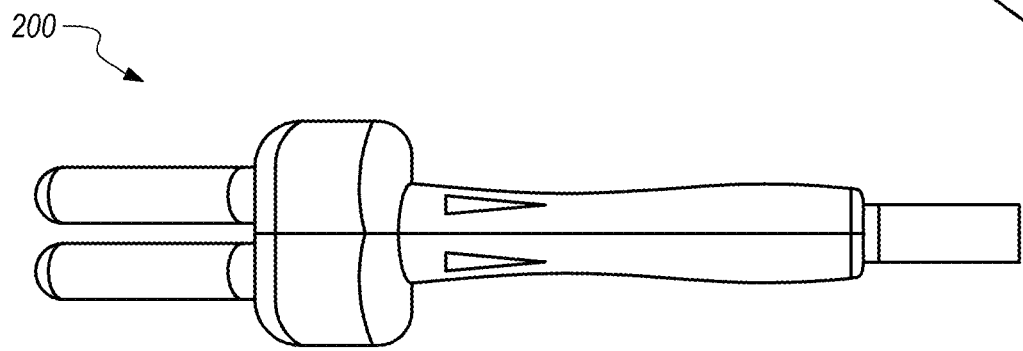
Figure 19E:
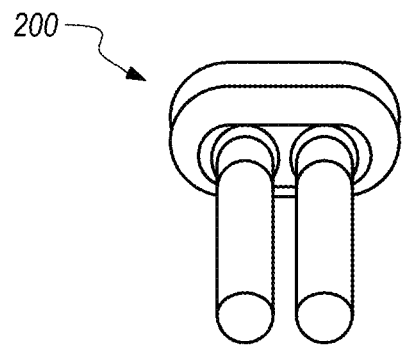
Figure 19F:
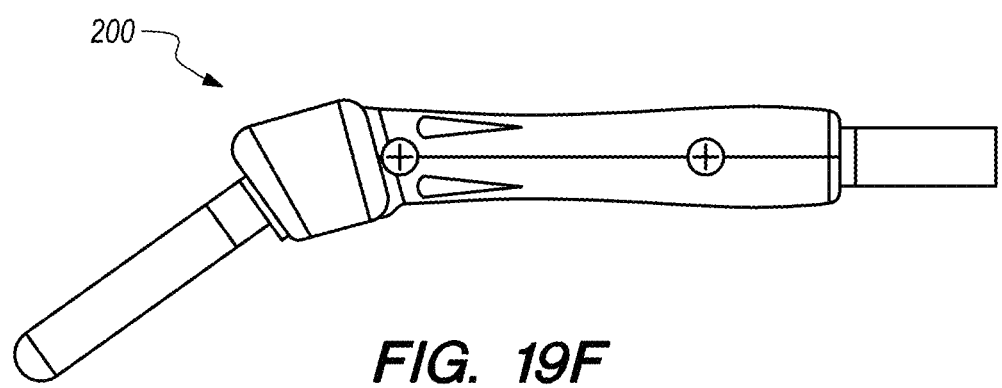
Figure 19G:
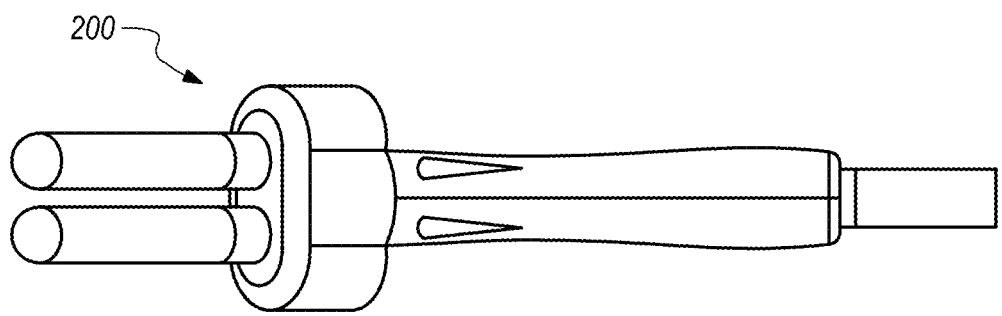

Referring to FIG. 17a-17f, shown are various angles of the first embodiment of a device 100 for use in conjunction with the substrates and methods of the present invention. FIGS. 18a and 18b show perspective views of the device 100 in the first embodiment. Specifically, FIG. 18a illustrates an exploded view of the device 100 comprised of cord 101 integrally connected to handle 109, handle 109 further connected to heat sink 102. Housing 103 securely connects to heat sink 102 thereby creating a cavity between the housing 103 and heat sink 102. Laser 104 is positioned within the cavity between housing 103 and heat sink 102. Male connectors 105 connect RF source 108 to housing 103 wherein threaded inserts 106 cover the connection therebetween. Cap 107 is positioned over housing 103 and secures to handle 109. FIG. 18c shows a detailed view of heat sink 102, laser 104, housing 103 and male connectors 105 in relation to each other. In a preferred embodiment, the device 100 may have a plurality of RF sources 108 wherein a plurality is defined as at least two tips (i.e. dipole). Housing 103 is capable of movement such that RF source 108 may be adjusted 45° up or down relative to the x-axis for ease of use depending upon the location of the wound receiving treatment.

The laser energy may have wavelength in the green wavelength range (520-570 nm), red wavelength range (620-750 nm), or yellow wavelength range (570-590 nm) having a wattage of 0.001 W to 5 W. In a preferred embodiment, laser energy has a wattage of 0.001 W to 5 W. The wattage is in the range of 0.001 W to 4 W, more preferred in the range of 0.003 to 3 W, and most preferred in the range of 0.005 W to 2 W. The RF energy may have a power of 9 watts or lower. The carrier wave frequency may be in the range of 0.1 MHz to 20 MHz while the non-sinusoidal waveform may be in the range of 0.5 to 40 KHz or from 0 to 24 GHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern. Optionally, the non-sinusoidal waveform may be single or multiple and in the range of the above parameters in the absence of a carrier wave.

Figures 20A, 20B:
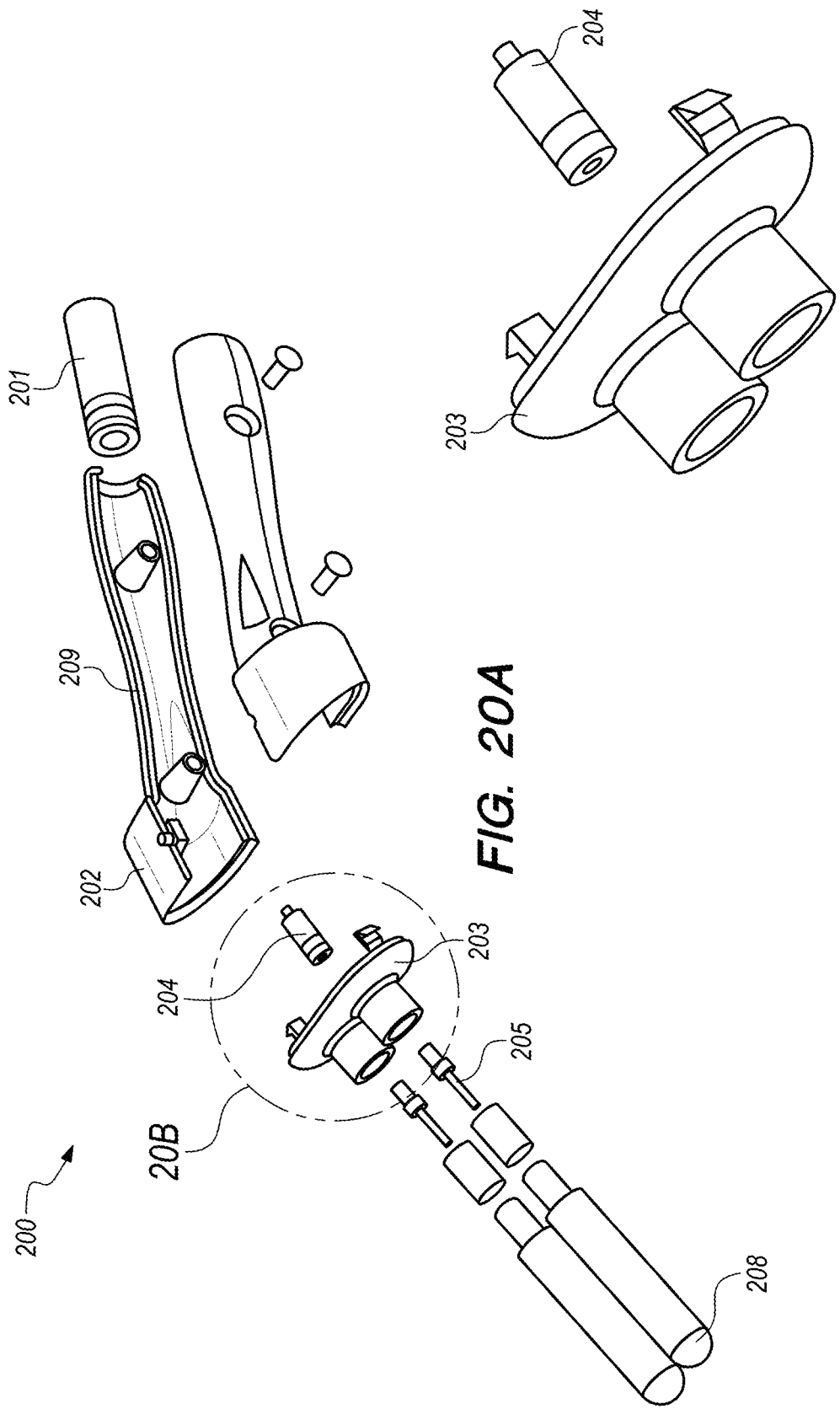

Referring to FIG. 19a-19g, shown are various angles of a second embodiment of a device 200 for use in conjunction with the substrates and methods of the present invention. FIG. 20a shows a perspective view of the device 200 of the second embodiment. Specifically, FIG. 20a illustrates an exploded view of the device 200 comprised of wire grommet 201 integrally connected to handle 209, handle 209 further comprised of heat sink 202. Housing 203 securely connects to heat sink 202 thereby creating a cavity between the housing 203 and heat sink 202. Laser 204 is positioned within the cavity between housing 203 and heat sink 202. Male connectors 205 connect RF source 208 to housing 203 wherein threaded inserts 206 cover the connection there between. FIG. 20b shows a detailed view of laser 204 and housing 203 in relation to each other.

Figure 21B:
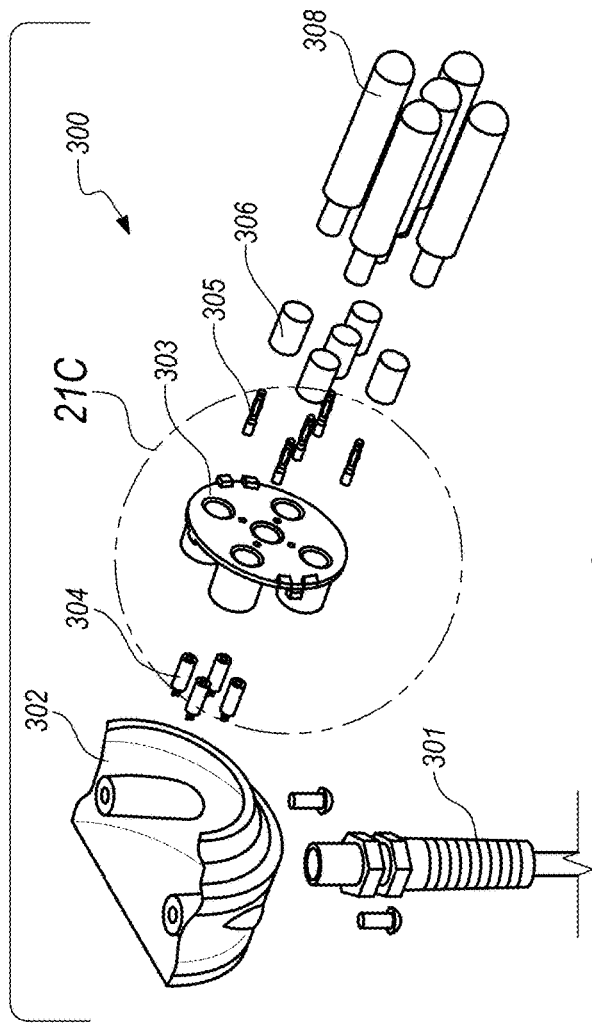
Figure 21C:
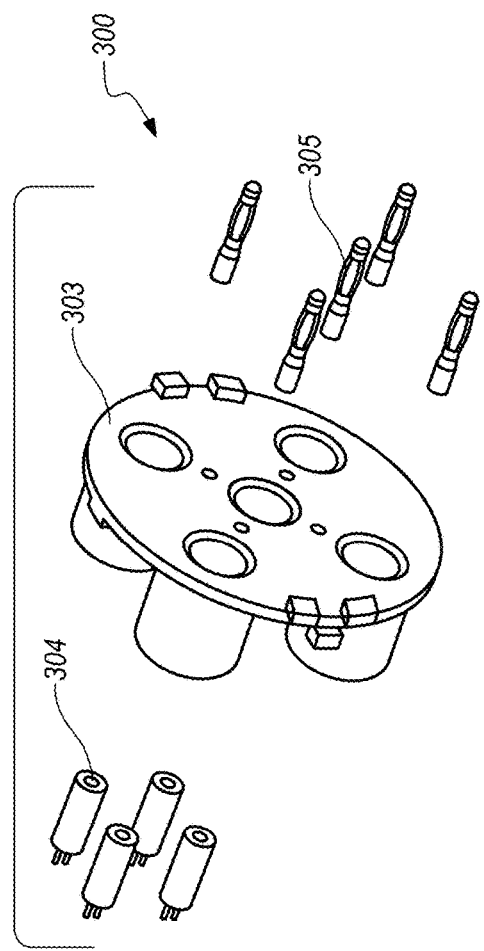
Figure 21A:
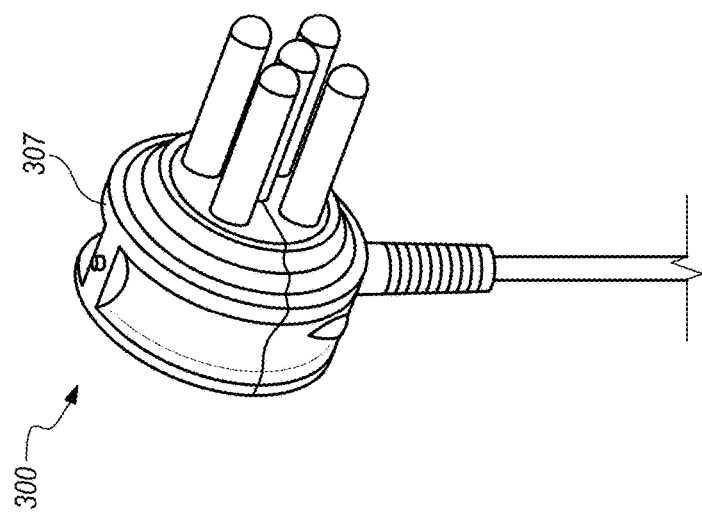

Referring to FIG. 21a-21c, shown is a third embodiment of a device 300 for use in conjunction with the substrates and methods of the present invention. FIG. 21a shows a perspective view of the device 300 of the second embodiment. Specifically, FIG. 21b illustrates an exploded view of the device 300 having an external housing 307 and further comprised of wire grommet 301 integrally connected to sub-housing 303, sub-housing 303 further comprised of heat sink 302. Sub-housing 303 securely connects to heat sink 302 thereby creating a cavity between the sub-housing housing 303 and heat sink 302. Laser 304 is positioned within the cavity between sub-housing housing 303 and heat sink 302. Male connectors 305 connect RF tips 308 to sub-housing housing 303 wherein threaded inserts 306 cover the connection there between. FIG. 21c shows a detailed view of laser 304 and sub-housing housing 303 in relation to each other. By way of example only, the device may have five or six tips.

Referring to FIG. 21d-21f, shown is a third embodiment of a device 300 for use in conjunction with the substrates and methods of the present invention. FIG. 21d shows a perspective view of the device 300 of the second embodiment. Specifically, FIG. 21e illustrates an exploded view of the device 300 comprised of wire grommet 301 integrally connected to sub-housing 303, sub-housing 303 further comprised of heat sink 302. Sub-housing 303 securely connects to heat sink 302 thereby creating a cavity between the sub-housing 303 and heat sink 302. RF tips 308 are positioned within the openings in close proximity to sub-housing 303. Male connectors 305 connect RF source 308 to sub-housing 303 wherein threaded inserts 306 cover the connection there between. FIG. 21f shows a detailed view sub-housing 303. By way of example only, the device may have five or six tips.

Referring to FIGS. 22a and 22b, shown is a fiber optic device 400 for use in conjunction with the substrates and methods of the present invention. Fiber optic device 400 is comprised of hand grip assembly 401 disposed between a first end and a second end. The first end is further comprised of nose insert 402 positioned between hand grip assembly 401 and removable nose assembly 404. Bent fiber tube 405 extends from removable nose assembly 405. The second end is further comprised of base insert 406 positioned between hand grip assembly 401 and rubber boot 407. Extending from rubber boot 407 is sheathed fiber 408 having a SMA connector 409 at the end opposite rubber boot 407.

Figure 22C:
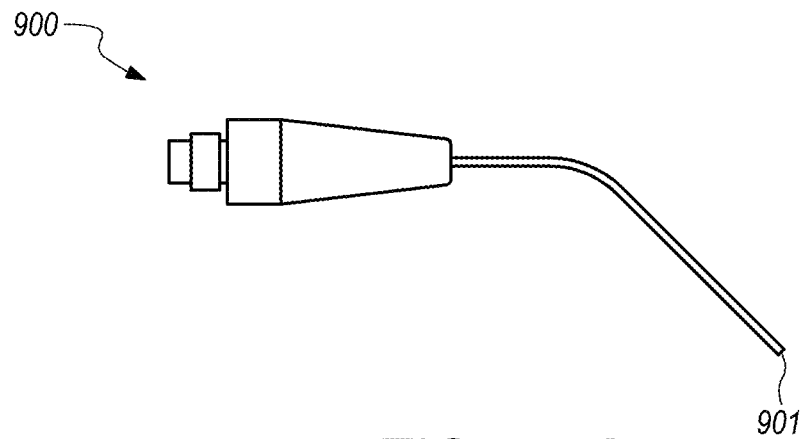
Figure 22D:
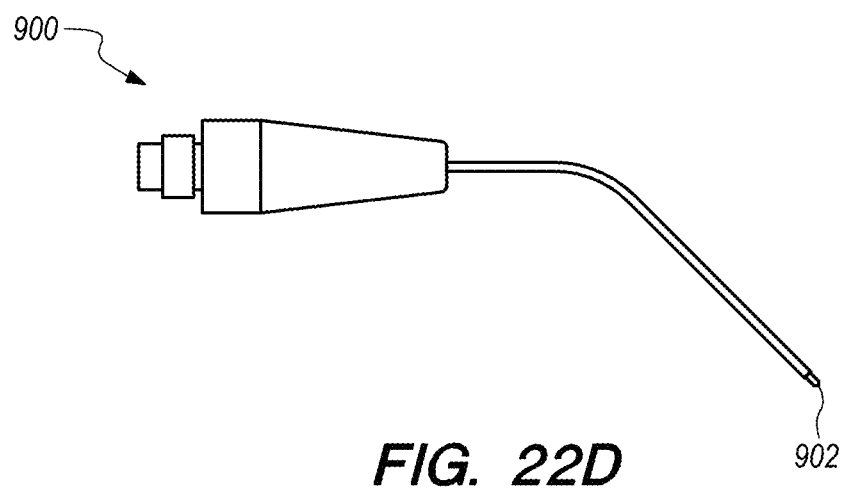

Referring to FIG. 22c-22d, shown are alternative embodiments of interchangeable fiber optic tips for a laser for use in conjunction with the substrates and methods of the present invention. FIG. 22c shows an interchangeable fiber optic tip for a laser having a nose piece 900 and a flat tip 901. FIG. 22d shows an interchangeable fiber optic tip for a laser having a nose piece 900 and a glass dispersion tip 902.

Figure 22E:
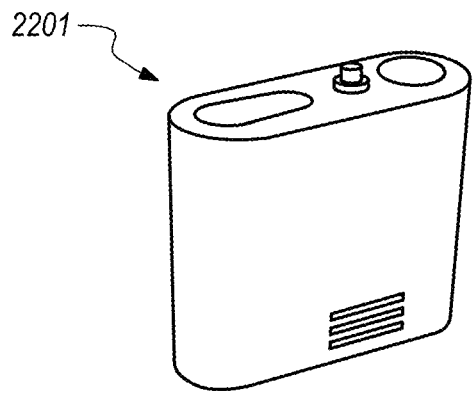
Figure 22F:
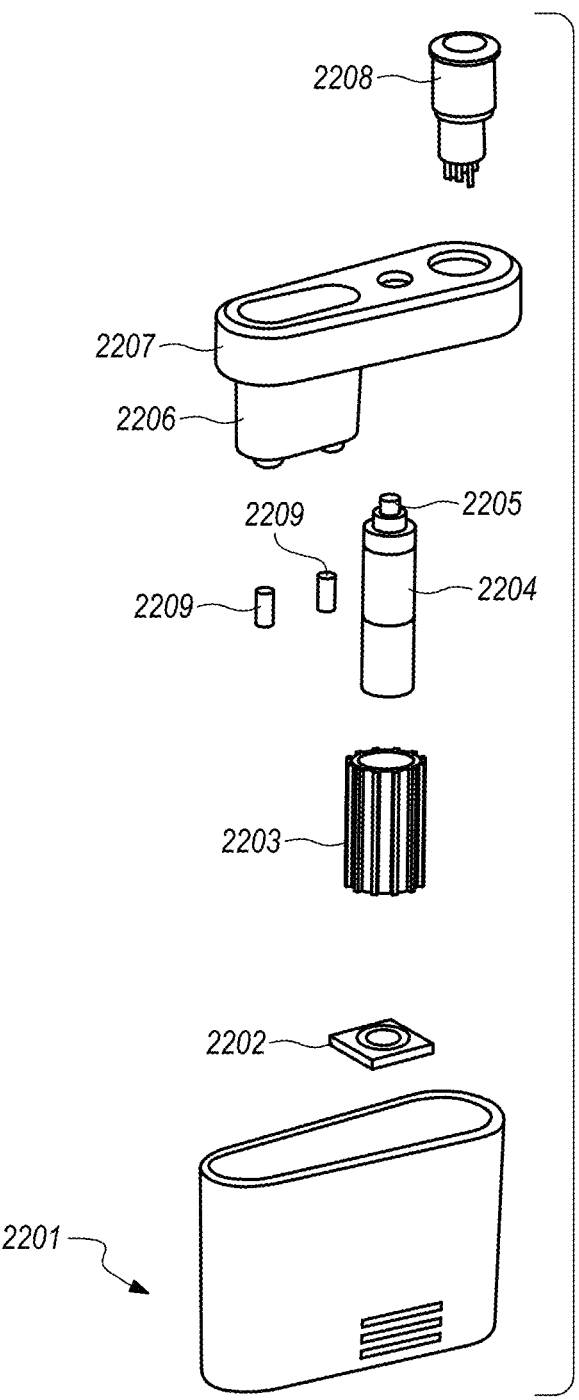

Referring to FIGS. 22e and 22f, shown are preferred embodiments of a power device suitable for accommodating the handpieces of the present invention. FIG. 22e shows a complete power device 2201. FIG. 22f shows an exploded view of the power device 2201 of FIG. 22e. The components include a heatsink 2203 positioned above a heatsink base 2202. A fiber optic laser 2204 sits above the heatsink 2203, wherein a fiber optic attachment 2205 sits above the fiber optic laser 2204 and is exposed through the top 2207 of the device 2201. A battery mount 2206 having device-side charging tips 2209 is positioned in order to accommodate a battery (not shown). A power switch 2208 appears through the top 2207 of the device 2201.

Figure 22G:
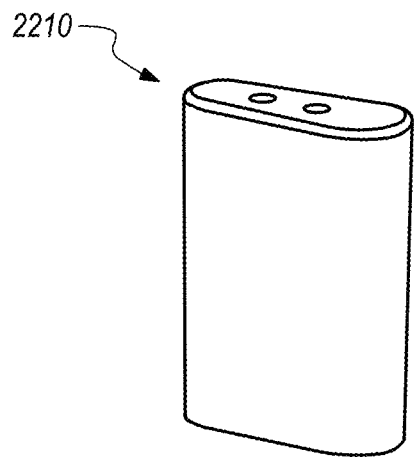
Figure 22H:
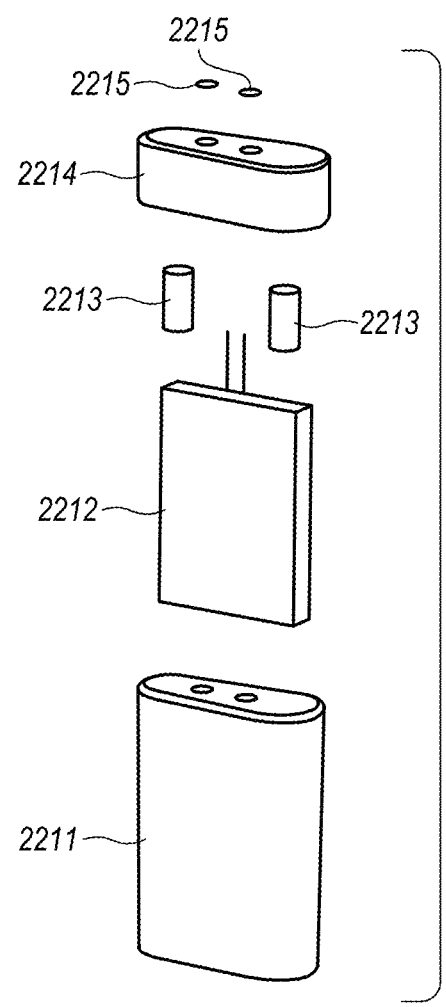
Figure 23A:
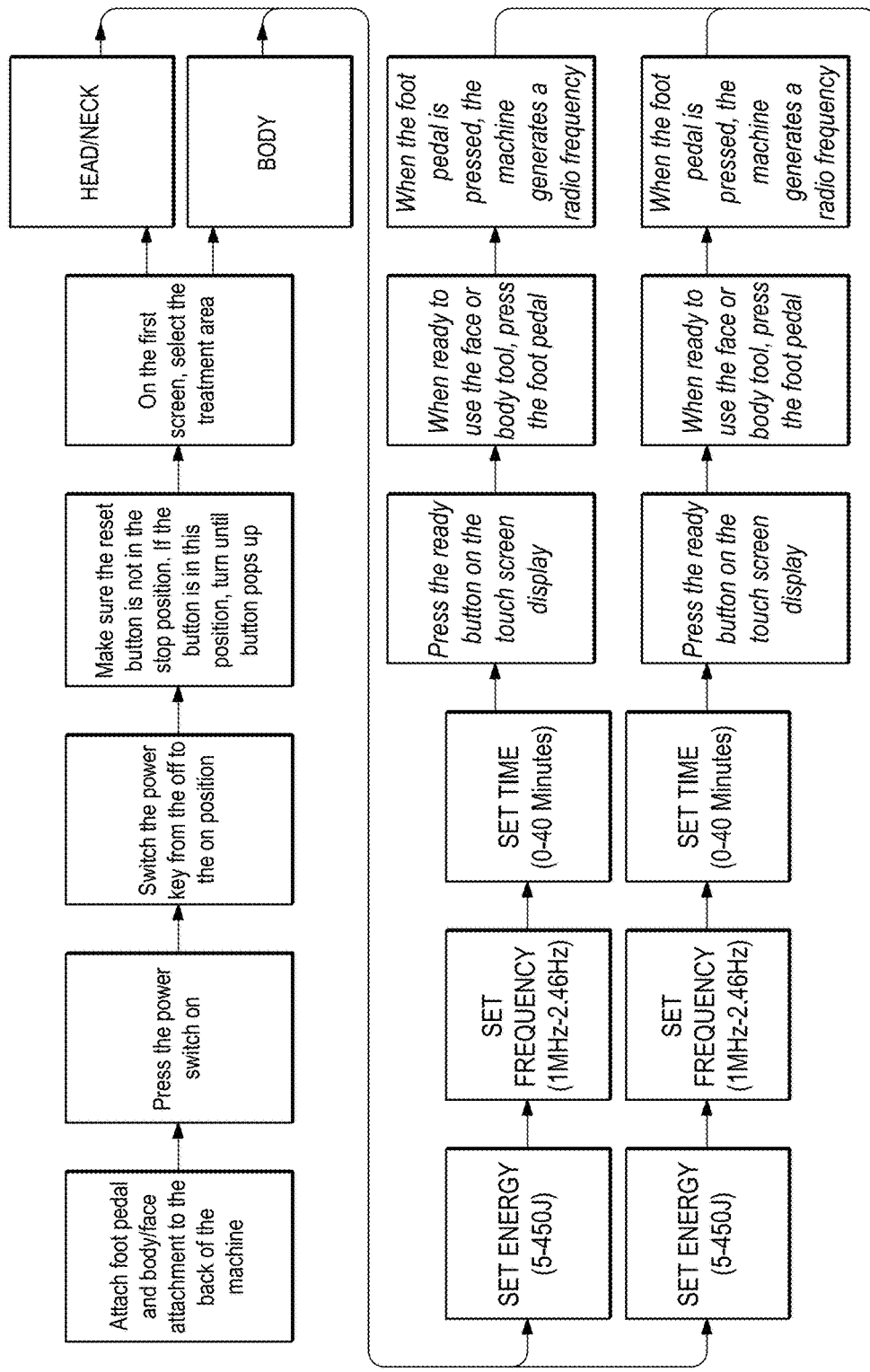
FIG. 23a-g shows flow charts of the protocol embodiments for using an RF device of the present invention, along with placement instrument embodiments for applying the preferred substrates of the present invention. (a) flow chart of the protocol along with certain parameters. (b) a preferred flow chart with preferred parameters. (c)-(e) oral surgery placement instruments. (f)-(g) periodontal placement instruments.
Figure 23B:
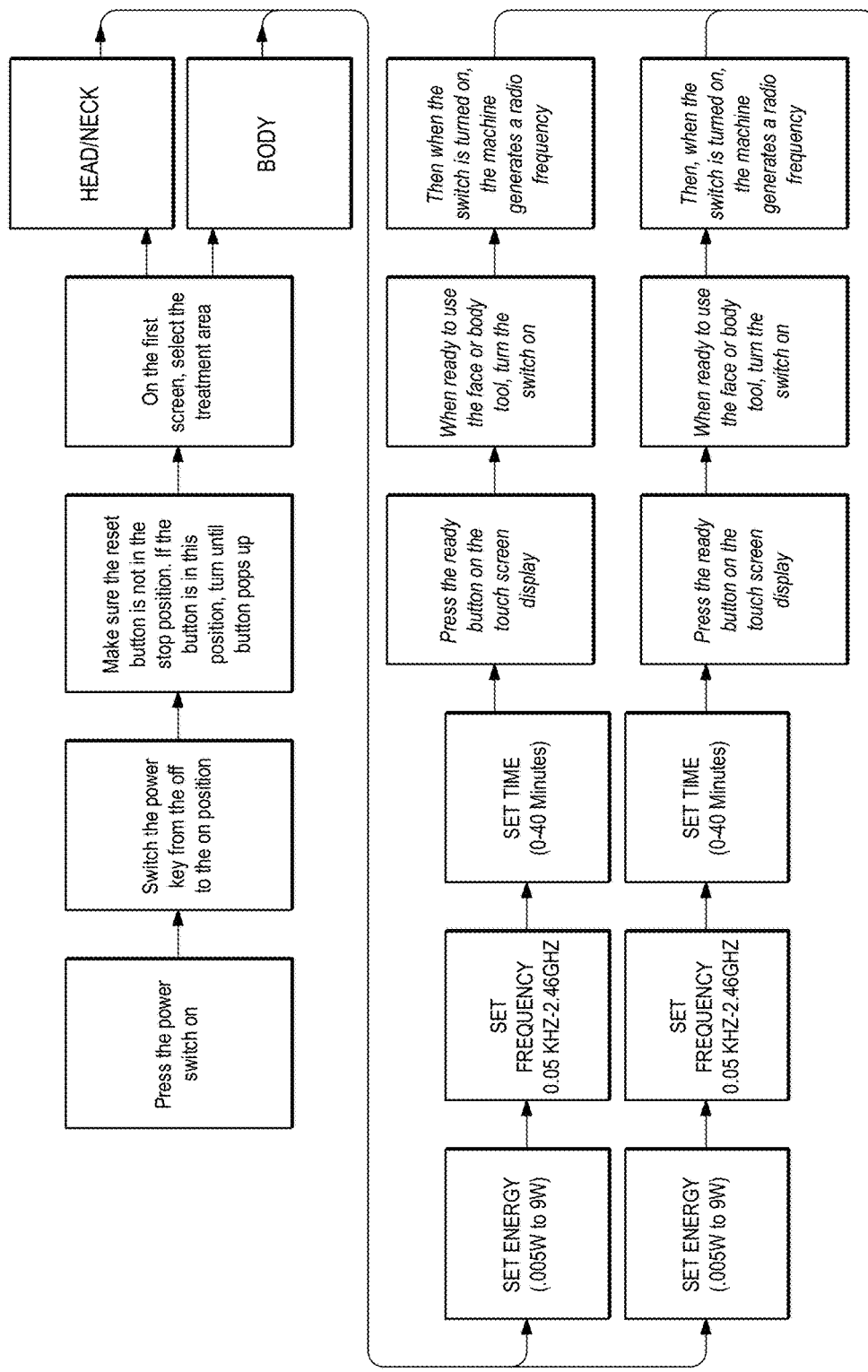
Figure 23C:
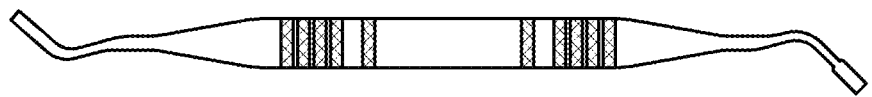
Figure 23D:
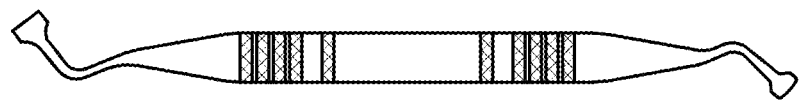
Figure 23E:
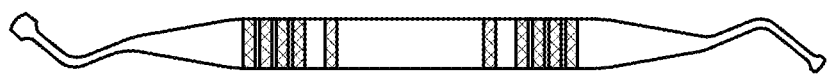
Figure 23F:
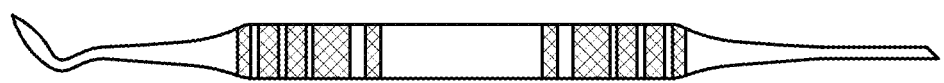
Figure 23G:
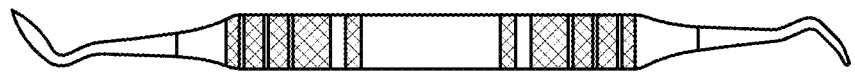

Referring to FIGS. 22g and 22h, shown are preferred embodiments of the battery pack for the power device for the handpieces of the present invention. FIG. 22g shows a battery pack 2210. FIG. 22h shows an exploded view of the battery pack 2210, including a base 2211 into which the battery 2212 is fitted. The battery 2212 is in contact with battery-side charging tips 2213 that abut charging housing 2215 through a top 2214 of the battery pack 2210.

Referring to FIGS. 23a-g, shown are flow charts and preferred instruments for placement of substrate for given procedures. FIGS. 22a and 22b detail specific protocols and certain parameters for operating the devices of the present invention. FIGS. 22c-22e detail certain placement instruments used in oral surgery procedures. FIGS. 22f and 22g describe certain placement instruments for use in periodontal procedures.

Firstly, the conditioner is applied to the root or bone surface. The root conditioner comprises the following at Table 1:

TABLE 1

| Component | |
|---|---|
| EDTA | 20-25 g. |
| Calcium gluconate | 10-20 g. |
| Methylparaben | .1-.9 g. |
| Propylparaben | .01-.1 g. |
| Ethanolamine | 2-8 mls. |
| Carboxymethylcellulose | 2-10 g. |
| Green food coloring | 1-2 drops |
| Sterile water | 100 mls. |

The conditioner is optionally rinsed out prior to application of additional substrates or laser light. Alternatively, the conditioner is left on the root or bone surface with the laser light being applied prior to application of any substrate. In an alternative embodiment, the conditioner is left in with only one substrate applied prior to application of the laser light. Optionally, the conditioner is left in the sulcus and substrate is added prior to any application of laser light.

The placement of the substrate into the sulcus containing luminesced blood enables the luminesced blood to coagulate upon the substrate.

Optionally, the liquid substrate or substrate 1 is comprised of the following, per 1 L of solution, at Table 2:

TABLE 2

| | % |
|---|---|
| Essential Amino Acids | |
| Isoleucine | 1.125 |
| Leucine | 1.125 |
| Methionine | 1.125 |
| Phenylalanine | 1.125 |
| Threonine | 1.125 |
| Tryptophan | 1.125 |
| Valine | 1.125 |
| Histidine | 1.125 |
| Lysine | 9 |
| Non-Essential Amino Acids | |
| Alanine | 0.25 |
| Arginine | 0.25 |
| Aspartate | 0.75 |
| Glutamate | 0.25 |
| Glycine | 0.25 |
| Serine | 0.25 |
| Proline | 9 |

TABLE 2-continued

| | % |
|---|---|
| Phosphates | |
| ADP | 0.667 |
| ATP | 0.667 |
| Acetylcholine | 0.667 |
| Free Bases | |
| Adenosine | 1.725 |
| Uridine | 1.725 |
| Guanosine | 1.725 |
| Cytidine | 1.725 |
| Benzoic Acid | 1 |
| Sodium Chloride | 1.1 |
| Sterile water | 60 |
| Total: | 100 |

Optionally, the total sterile water component is adjusted 20% up or down, depending on the desired viscosity to be achieved.

Optionally, the sterile water component also contains some amount of Hyaluronic Acid.

In an alternative embodiment, the liquid substrate or substrate 1 is comprised of the following, at Table 3:

TABLE 3

| | Grams |
|---|---|
| Essential Amino Acids | |
| Isoleucine | 11.25 |
| Leucine | 11.25 |
| Methionine | 11.25 |
| Phenylalanine | 11.25 |
| Threonine | 11.25 |
| Tryptophan | 11.25 |
| Valine | 11.25 |
| Histidine | 11.25 |
| Lysine | 90 |
| Non-Essential Amino Acids | |
| Alanine | 2.5 |
| Arginine | 2.5 |
| Aspartate | 7.5 |
| Glutamate | 2.5 |
| Glycine | 2.5 |
| Serine | 2.5 |
| Proline | 90 |
| Phosphates | |
| ADP | 7-8 |
| ATP | 7-8 |
| Acetylcholine | 6-7 |
| Free Bases | |
| Adenosine | 13-14 |
| Uridine | 13-14 |
| Guanosine | 13-14 |
| Cytidine | 13-14 |
| Iridine | 13-14 |
| Benzoic Acid | 20 |
| Sodium Chloride | .1-.9 |
| Sterile water | .9-1.2 L |

In an alternative embodiment, an additional substrate may be applied, the additional substrate, substrate 2, comprised of dense or porous tricalcium phosphate comprising of one size or variety of sizes of crystals: 4-50 µm, 50-150 µm, 100-300 µm, 500-1000 µm, 1-3 mm, and 3-6 mm and hydroxyapatite crystals.

In an alternative embodiment, an additional substrate may be applied, the additional substrate, substrate 3, is comprised of the following at Table 4:

TABLE 4

| | Grams |
|---|---|
| Hyaluronic acid | 200 mg to 5.1 g |
| Fatty acids | |
| Linoleic acid (LA) | 4 |
| Alpha-linolenic acid (ALA) | 4 |
| | 8 |
| Sugars (except glucose and fucose) | |
| Mannose | 0.6 |
| Galactose | 0.6 |
| N-acetylgalactosamine | 0.6 |
| N-acetylglucosamine | 0.6 |
| N-acetylneuraminic acid | 0.6 |
| Fucose (L config. and no carboxyl at 6 position) | 0.6 |
| Xylose | 0.6 |
| | 4.2 |
| Glucose | 1.1 |
| Fucose (L config. and no carboxyl at 6 position) | 1.1 |
| Lipids | |
| A | 0.3 |
| D2 | 0.3 |
| D3 | 0.3 |
| E | 0.3 |
| K1 | 0.3 |
| K2 | 0.3 |
| B12 (Methylcobalamin) | 0.3 |
| B12 (Nydroxocobalamin) | 0.3 |
| Cholesterol | 0.3 |
| Diaglycerol | 0.3 |
| | 3.0 |
| Vitamins | |
| B1 | 0.3 |
| B2 | 0.3 |
| B3 | 0.3 |
| B5 | 0.3 |
| B6 | 0.3 |
| B7 | 0.3 |
| B9 | 0.3 |
| C | 0.3 |
| Pantothenic acid | 0.3 |
| | 2.7 |
| Electrolyte Sources | |
| Calcium chloride | .5 |
| Choline Chloride | .5 |
| Magnesium Sulfate | .5 |
| Potassium Chloride | .5 |
| Potassium Phosphate-monobasic | 1 |
| Sodium Bicarbonate | .5 |
| Sodium Chloride | .5 |
| Sodium Iodide | .5 |
| | 4.5 |
| Metals | |
| Ag nanoparticles | 0.3 |
| Au nanoparticles | 0.3 |
| | 0.6 |

TABLE 4-continued

|  | Grams |
| --- | --- |
| Iconic metals | |
| Copper | 0.3 |
| Zinc | 0.3 |
| Selenium | 0.3 |
| Iron | 0.3 |
| Manganese | 0.3 |
| Cobalt | 0.3 |
| Chromium | 0.3 |
| Boron | 0.3 |
| Molybdenum | 0.3 |
|  | 2.7 |
| Other ionic metals | |
| Boron | 0.3 |
| Silicon | 0.3 |
| Nickel | 0.3 |
| Vanadium | 0.3 |
|  | 1.2 |
| Benzoic Acid | Up to 10.1 |
| Sodium Chloride | .1-.9 |
| Sterile water | 60-300 ml |

Optionally, the total sterile water component is adjusted 20% up or down, depending on the desired viscosity to be achieved.

In an alternative embodiment, an additional substrate may be applied, the additional substrate, substrate 4, is comprised of the following at Table 5:

TABLE 5

|  | Grams | Notes |
| --- | --- | --- |
| Component | | |
| carbomer | 10-40 | For acute wound (see FIG. 39) use 10-20 |
|  |  | For chronic wound (see FIG. 38) use 25-40 |
| Electrolytes | | |
| Potassium chloride | 0.5-3 | |
| Chloride | 0.1-1 | |
| Sodium | 0.1-1 | |
| Potassium | 0.1-1 | |
| Manganese | 0.1-1 | |
| Calcium tri-Phosphate | 0.5-4 | |
| Sulfate | 0.1-1 | |
| Bicarbonate | 0.1-1 | |
| Snail serum |  | 50-150 ml; for chronic wounds substrate 6 may be incorporated (see FIG. 41); decreases depending of volume of substrate 6 |
| Snail secretion filtrate | 50-150 mg | |
| HA | 3-6 | |
| Au | 0.1-1 | |
| Ag | 0.1-1 | |
| Cu | 0.1-1 | |
| Fe | 0.1-1 | |
| Pt | 0.1-1 | |
| Collagen | 50-150 | |
| fucose | 0.5-1 | |
| Glyceine HCl | 0-0.4 | |

Figure 40:
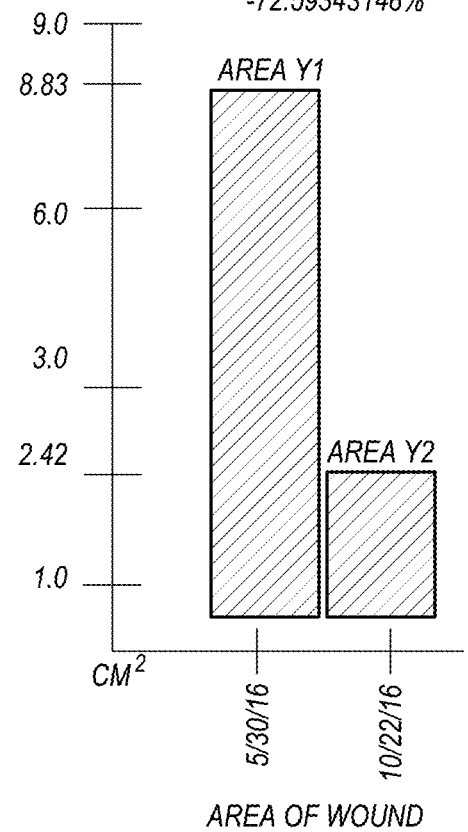
FIG. 40 shows ankle wound size reduction before and after treatment.

Metals may be increased 50% for chronic wounds (see FIG. 40).

Optionally, the total sterile water component is adjusted 20% up or down, depending on the desired viscosity to be achieved.

Substrates may have different modalities of delivery, for example; liquid, gel, drops, sprays, injections or intravenous having the same ingredients, as well as sublingual, anal, foam and ointment formulations or drinkable liquids.

In an alternative embodiment, an additional substrate may be applied, the additional substrate 5 is comprised of the following:
1. collagen, limed and/or
2. collagen, unlimed, and/or
3. collagen, supplemented with porous tricalcium phosphate crystals with one size or variety of sizes: 4-50 μm, 50-150 μm, 100-300 μm, 500-1000 μm, 1-3 mm and 3-6 mm. The tricalcium phosphate crystals may be dense or porous. Optionally, substrate 5 may be used in the absence of other substrates.

In an alternative embodiment, an additional substrate may be applied, the additional substrate 6 is comprised of the following:
1. collagen, limed and/or
2. collagen, unlimed and/or
3. HCl and/or
4. NaCl and/or
5. Cu, Ag, Fe, Au, Pt or any combination thereof and/or
6. Collagen, supplemented with porous tricalcium phosphate crystals with one size or variety of sizes: 4-50 μm, 50-150 μm, 100-300 μm, 500-1000 μm, 1-3 mm and 3-6 mm. The tricalcium phosphate crystals may be dense or porous. Optionally, substrate 6 may be used in the absence of other substrates.
7. nanoparticles wherein the nanoparticles are chosen from the group consisting of copper, Au, Ag, iron, $Fe_3O_4$, and platinum or any combination thereof and/or
8. compounds wherein the compounds are chosen from the group consisting of $CuCl_3$, $CuCl_2$, $CuCl$, $FeCl_3$, $FeCl_2$, $AuCl$, $AuCl_2$, $AuCl_3$, $AgCl$, $AgCl_2$ or any combination thereof, and/or
9. Hyaluronic Acid and/or
10. Hydroxyapetite, crystals, dense or porous and in a variety of crystal sizes.

An additional substrate may be applied, the additional substrate comprised of the following: a mixture of tricalcium phosphate and hydroxyapatite crystals. The tricalcium phosphate is precipitated prepared with HCL CaOH/devil's claw oil, in a preferred embodiment. Optionally, the additional substrate includes 50% tricalcium phosphate prepared with 50% hydroxyapatite crystals. The tricalcium phosphate crystals used are granules in the following sizes: 4-50 μm, 50-150 μm, 100-300 μm, 500-1000 μm, 1-3 mm and 3-6 mm. The tricalcium phosphate crystals may be dense or porous.

The additional substrate may be comprised of hydroxyapatite crystals of granules containing the following sizes: 10-50 μm, 50-150 μm, 100-300 μm, 500-1000 μm, 1-3 mm and 3-6 mm. The hydroxyapatite crystals may be dense or porous.

In the following examples, the conditioner is applied and subsequently rinsed out. Optionally, the conditioner is left in the sulcus.

After the conditioner is applied, the sulcus is biostimulated with a laser light. After this occurs, the liquid substrate is applied. Optionally, the additional substrate is applied. For cavities other than oral cavities, a diluted substrate assists treatment when ingested or taken via IV is beneficial although not required.

In an alternative embodiment, an optional spray substrate, spray 1, may be applied, the spray comprised of the following: Au, and/or Ag, and/or Cu, and/or Fe, and/or Pt, and sterile water.

In an alternative embodiment, an optional spray substrate, spray 2, may be applied, the spray comprised of the following: Cl, Na, K, Mg, Phosphate, Sulfate, bicarbonate and sterile water.

The fiber optic device of the present invention is the preferable device placed inside the sulcus for treatment. Optionally more than one fiber can be in the handpiece and each fiber can be of a different wavelength and different average power. The sulcus or wound may also be treated with laser, RF or laser with RF or LED. The remaining disclosed embodiments of the device may be used in wound treatment in conjunction with the substrates depending on the wound site and severity of the wound. Substrates disclosed herein may be a form including, but not limited to, liquid, tablet, enema, gel, injection or foam.

Alternative RF and/or Laser Assisted Wounded Tissue Regeneration:
1. Optionally scale/root plane;
2. Optionally etch root of tooth or implant;
3. Rinse with saline water;
4. Optionally place tip of laser, LED or RF into or around the sulcular or any other wound, and turn the laser on for up to 5 seconds or more;
5. Repeat step 4 circumferentially vertically and horizontally around tooth or implant until the entire wound has been saturated by energy;
6. Place Substrate 1, and/or 2, and/or 3, and/or 4 and/or 5 and/or 6 into glass dappen dishes;
7. Mix the desired amount of substrate 1, and/or 2 and/or 3 and/or 4 and/or 5 and/or 6 in dappen dish;
8. Place the desired mixture into the sulcular wound or wound where bone/tissue loss occurred;
9. Wait a few seconds;
10. Place more of the mixture into the sulcular wound where bone/tissue damage occurred if necessary;
11. Wait a few seconds;
12. Repeat steps 8 until all defects have been filled;
13. Wait 1 minute;
14. Optionally place hand piece with its laser and/or RF tip and/or LED tip, with or without laser, in proximity to the wound, turn on and keep in position for 1 minute;
15. Wait 10 seconds; and
16. Repeat RF step 14 until entire wound has been covered with energy and without laser.

Alternative RF and/or Laser Assisted Wounded Tissue Repair:
1. Optionally cleanse wound with saline;
2. Place any substrate or any combination of substrates onto or into wound;
3. Direct RF/laser, RF, LED, or laser energy at wound for 1 minute or longer;
4. Place another layer of a chosen substrate or any combination of substrates onto or into wound if necessary;
5. Wait 10 seconds;
6. Repeat steps 2-5 until wound bed is covered; and
7. Alternatively wait a specified period of time in between step 2-6.

Treatment of the oral cavity, head/neck, tongue, anal, vaginal region and the deeper or surrounding areas reached while treating these may be performed with the RF with substrate (applied substrate or drank with water), RF without substrate, RF plus laser with substrate (applied substrate or drank with water), RF plus laser without substrate and laser with substrate (applied substrate or drank with water), laser without substrate. The treatment described may be utilized throughout the gastrointestinal tract, head/neck and anus.

The laser, RF or LED treatment applied to the oral cavity and surrounding structures, anal cavity and its surrounding structures, head and neck region and its surrounding structures has benefits in deeper areas of the structures. Those deeper areas of the corresponding structures are thus part of the treatment site. Surrounding structures include, but are not limited to, all bone, cartilage, muscles, tendons, nerves, blood vessels, epithelium and fascia.

RF and/or Laser Assisted Head and Neck Wound Tissue Repair:
1. Optionally drink 4 oz. diluted Substrate 1;
2. Wait 15 minutes;
3. Optionally drink 4 oz. diluted Substrate 3;
4. Wait 15 minutes;
5. Direct RF/laser, RF or laser energy at head and neck location and the surrounding structures where wound occurred;
6. Keep energy in place or move over desired area until desired effect achieved; and
7. Move on to next site until desired result achieved.
8. Procedure can be started at Step 1 or Step 5.

Surrounding structures include, but are not limited to, all bone, cartilage, muscles, tendons, nerves, blood vessels, and epithelium.

Head and neck includes, but is not limited to, all structures of the head and neck including esophagus and its surrounding structures, mouth including all interior mouth structures such as tongue (entire area of tongue including but not limited to anterior, posterior, dorsal, ventral, and sublingual), floor of mouth including but not limited to arterial and nerve beds, linea alba, buccal mucosa, buccal flanges, lingual flanges, nose, interior of nose (including but not limited to the epithelial lining), all muscles and other structures of the tongue and surrounding the tongue, all muscles of the eye and surrounding the eye, all arterial, venous and nerve beds of the eye and surrounding the eye. All muscles, nerves, veins, all glands, soft and hard tissue of the head and neck, and any other structure of the head and neck.

RF and/or Laser Assisted Vaginal Wound Repair:
1. Optionally drink 4 oz. diluted Substrate 1;
2. Wait 15 minutes;
3. Optionally drink 4 oz. diluted Substrate 2;
4. Wait 15 minutes;
5. Direct RF/laser, RF or laser energy at the vagina and its surrounding structures;
6. Keep energy in place for 10-20 minutes or until desired effect achieved;
7. Rotate hand piece; and
8. Repeat steps 5-7 until desired result achieved.
9. Procedure can be started at Step 1 or Step 5.

Surrounding structures include, but are not limited to, all bone, cartilage, muscles, tendons, nerves, blood vessels, and epithelium.

RF and/or Laser and/or LED Assisted Wound/Tissue Repair—Sphincter Ani Externis:
1. Direct RF/laser, RF or laser energy at the anus and its surrounding structures;
2. Keep energy in place until desired effect achieved;
3. Rotate hand piece if necessary
4. Repeat steps 1-4 until desired result achieved.

Surrounding structures include, but are not limited to, all bone, cartilage, muscles, tendons, nerves, blood vessels, and epithelium and any other structures of the anal cavity.

RF and/or Laser Assisted Wound Repair/Tissue Repair—Breast:
1. Optionally drink 4 oz. diluted Substrate 1, and/or 2, and/or 3, and/or 4, and/or 5;
2. Wait 15 minutes;
3. Optionally drink 4 oz. diluted Substrate 1, and/or 2, and/or 3, and/or 4, and/or 5;
4. Wait 15 minutes;
5. Direct RF/laser, RF or laser energy at the breast and structures related to the breast;
6. Keep energy in place for 10-20 minutes or until desired effect achieved;
7. Rotate hand piece; and
8. Repeat steps 5-7 until desired result achieved.
9. Procedure can be started at Step 1 or Step 5.

Related structures include, but are not limited to, all bone, cartilage, muscles, tendons, nerves, blood vessels, lymph nodes and epithelium.

RF and/or Laser Assisted Wound/Tissue Repair, Tongue and its Supporting Structures in the Swallowing Mechanism:
1. Optionally drink 4 oz. diluted Substrate 1, and/or 2, and/or 3, and/or 4, and/or 5;
2. Wait 15 minutes;
3. Optionally drink 4 oz. diluted Substrate 1, and/or 2, and/or 3, and/or 4, and/or 5;
4. Wait 15 minutes;
5. Direct RF/laser, RF or laser energy at tongue and its surrounding structures;
6. Keep energy in place for 10-20 minutes or until desired effect achieved;
7. Rotate hand piece if necessary; and
8. Repeat steps 5-7 until desired result achieved.
9. Procedure can be started at Step 1 or Step 5.

Surrounding structures include, but are not limited to, all bone, cartilage, muscles, tendons, nerves, blood vessels, and epithelium.

RF and/or Laser Assisted Wound/Tissue Repair, Tongue and its Supporting Structures in the Swallowing Mechanism:
1. Direct RF/laser, RF or laser energy at tongue and its surrounding structures lingually, labially, sublingually, pharyngeally or buccally;
2. Keep energy in place for until desired effect achieved;
3. Rotate hand piece if necessary; and
8. Repeat steps 1-3 until desired result achieved.

Surrounding structures include, but are not limited to, all bone, cartilage, muscles, tendons, nerves, blood vessels, and epithelium.

RF and/or Laser Assisted Wound Regeneration:
1. Optionally drink 4 oz. diluted Substrate 1, and/or 2, and/or 3, and/or 4, and/or 5 and/or 6;
2. Wait 15 minutes;
3. Optionally drink 4 oz. diluted Substrate 1, and/or 2, and/or 3, and/or 4, and/or 5 and/or 6;
4. Wait 15 minutes;
5. Optionally direct RF/laser, RF, LED or laser energy at wound and its surrounding structures;
6. Apply or place Substrate 1, and/or 2, and/or 3, and/or 4, and/or 5 and/or 6;
7. Optionally direct RF/laser, RF, LED or laser energy at wound and its surrounding structures;
8. Keep energy in place for up to 10-20 minutes or until desired effect achieved;
9. Rotate energy source if necessary; and
10. Repeat steps 5-9 until desired result achieved.
11. Alternatively wait a week in between steps 5-9 and gradually cover wound bed.
12. Procedure can be started at Step 1 or Step 5.

Surrounding structures include, but are not limited to, all bone, cartilage, muscles, tendons, nerves, blood vessels, and epithelium.

RF and/or Laser Assisted Pore Repair:
1. Optionally drink 4 oz. diluted Substrate 1, and/or 2, and/or 3, and/or 4, and/or 5;
2. Wait 15 minutes;
3. Optionally drink 4 oz. diluted Substrate 1, and/or 2, and/or 3, and/or 4, and/or 5;
4. Wait 15 minutes;
5. Direct RF/laser, RF or laser energy at pores and their surrounding structures;
6. Keep energy in place for 10-20 minutes or until desired effect achieved;
7. Rotate hand piece; and
8. Repeat steps 5-7 until desired result achieved.
9. Procedure can be started at Step 1 or Step 5.

Surrounding structures include, but are not limited to, all bone, cartilage, muscles, tendons, nerves, blood vessels, and epithelium.

RF and/or Laser and/or LED Assisted Oral Cavity Wound Repair:
1. Optionally drink 4 oz. diluted Substrate 1, and/or 2, and/or 3, and/or 4, and/or 5 and/or 6;
2. Wait 15 minutes;
3. Optionally drink 4 oz. diluted Substrate 1, and/or 2, and/or 3, and/or 4, and/or 5 and/or 6;
4. Wait 15 minutes;
5. Optionally direct RF/laser, RF or laser energy at oral cavity and its' surrounding structures;
6. Optionally apply Substrate 1, and/or 2, and/or 3, and/or 4, and/or 5 and/or 6;
7. Optionally direct RF/laser, RF, LED or laser energy wound and its surrounding structures;
8. Keep energy in place for 10-20 minutes or until desired effect achieved;
9. Rotate energy source; and
8. Repeat steps 5-9 until desired result achieved.
9. Procedure can be started at Step 1 or Step 5.

Surrounding structures include, but are not limited to, all bone, cartilage, muscles, tendons, nerves, blood vessels, and epithelium.

Further still, wound treatment may be utilized for additional conditions including, but not limited to, vaginal wound repair, breast wound repair/regeneration/generation, anal wound repair, age spot repair, pore repair, skin and tissue repair and general body wound repair.

Figure 33A:
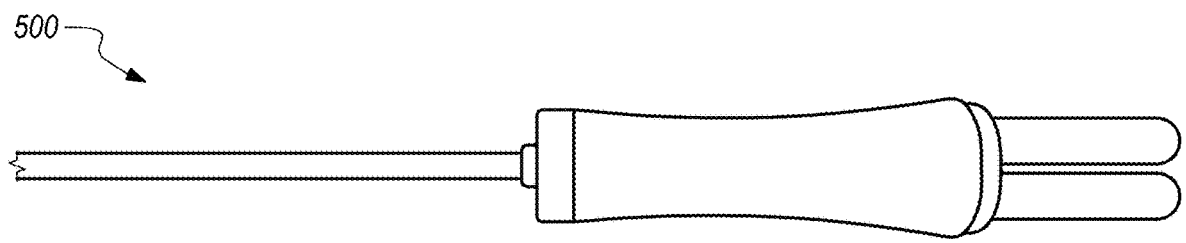
FIG. 33*a*-33*e* show various views of an RF hand piece of the present invention. (a) shows a top view. (b) shows a side view. (c) shows a perspective view of the RF tips. (d) shows an exploded side perspective view. (e) shows an alternative side perspective view.
Figure 33B:
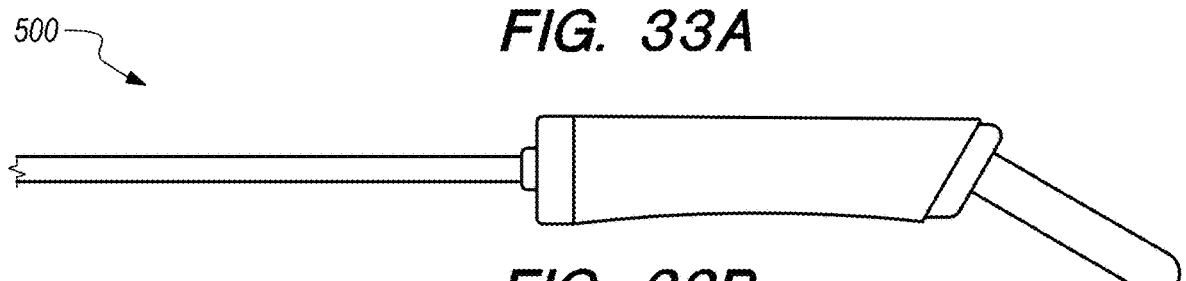
Figure 33C:
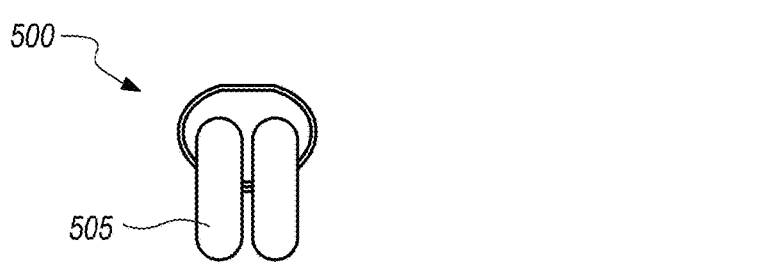
Figure 33D:
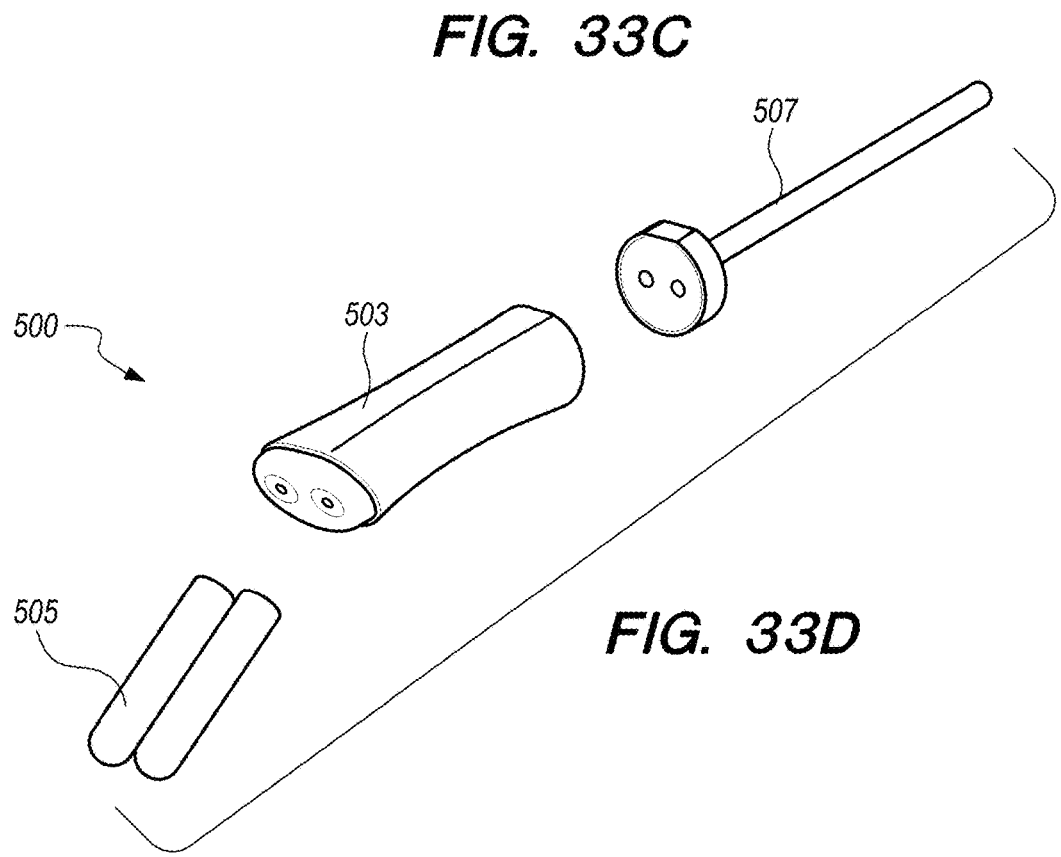
Figure 33E:
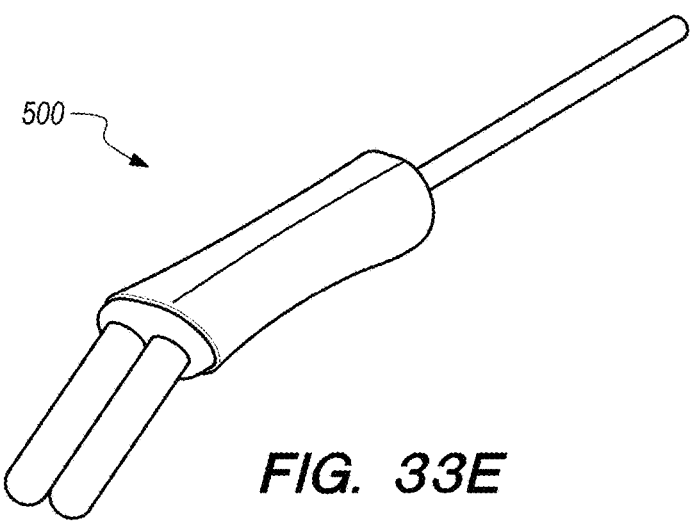

Referring to FIG. 33a-33e, shown is a fourth embodiment of a device 500 for use in conjunction with the substrates and methods of the present invention. FIG. 33a shows a top view of the device 500 of the fourth embodiment. FIG. 33b shows a side view and FIG. 33c shows a close-up of the tip of device 500. Specifically, FIG. 33d illustrates an exploded view of the device 500 comprised of housing 503, tips 505 and energy source 507. Energy source 507 provides RF energy to housing 503 when connected. FIG. 33e shows a side perspective view of the assembled device 500. Optionally, the device 500 may be used in the absence of substrates.

Figure 34A:
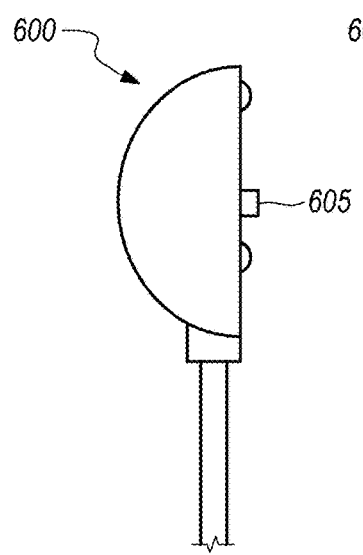
FIG. 34*a*-34*f* show various views of a fourth alternative diode laser of the present invention. (a) shows a right side view. (b) shows a front view. (c) shows a left side view. (d) shows a left side perspective view. (e) shows a top view. (f) shows a right side perspective view.
Figure 34B:
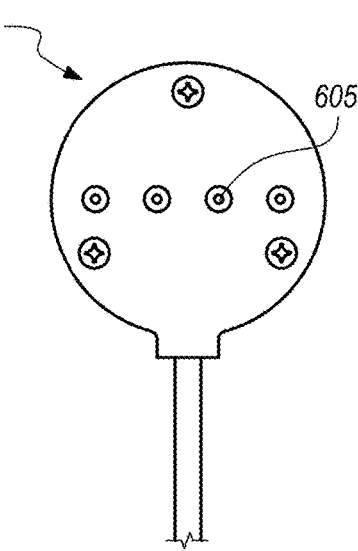
Figure 34C:
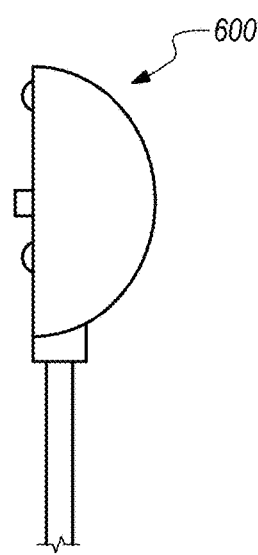
Figure 34D:
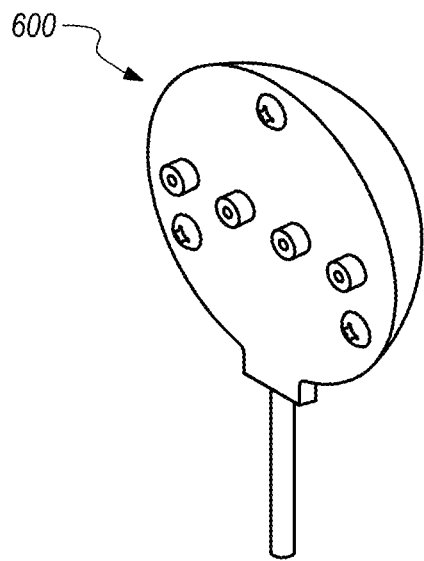
Figure 34E:
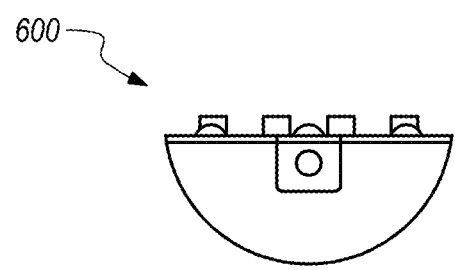
Figure 34F:
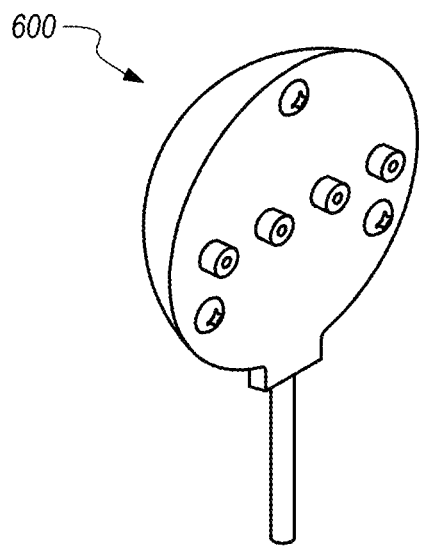

Referring to FIG. 34a-34f, shown is a fifth embodiment of a device 600 for use in conjunction with the substrates and methods of the present invention. FIGS. 34d and 34f show side perspective views of device 600. FIG. 34a shows a side view of device 600 wherein device 600 has a hemispheric shape and is further comprised of a flat surface opposite the hemispheric surface. The flat surface is further comprised of a plurality of mini lasers 605 for delivery of diode laser energy for treatment of an acute wound. The mini lasers 605 are self-contained within device 600. In a preferred embodiment, the laser power used for treatment may be approximately 6-24 mW.

Figure 35A:
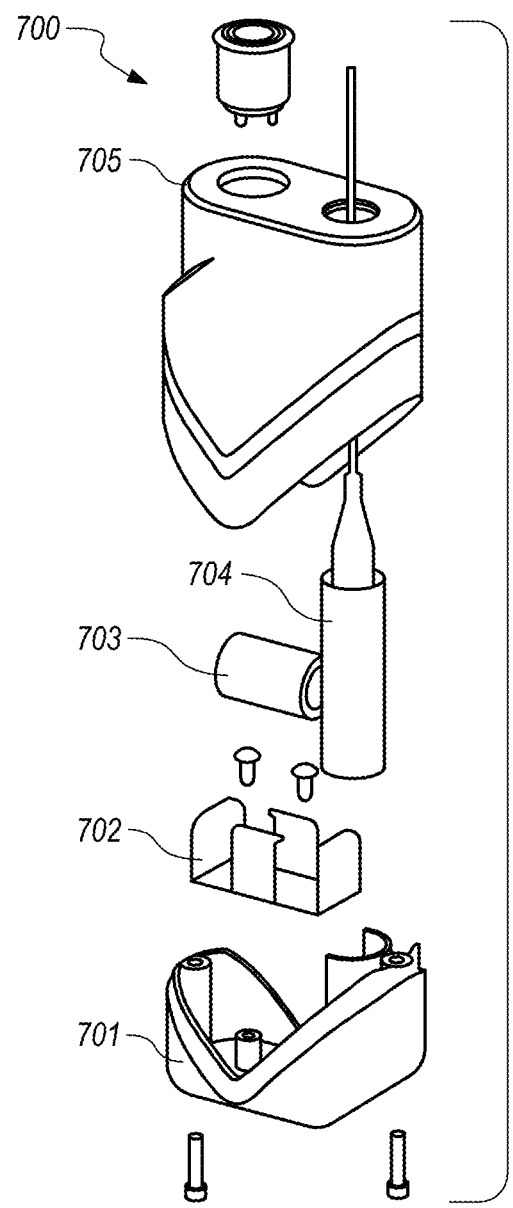
FIG. 35 show various views of a laser power source for the fiber optic hand piece and interchangeable tips.
Figure 35B:
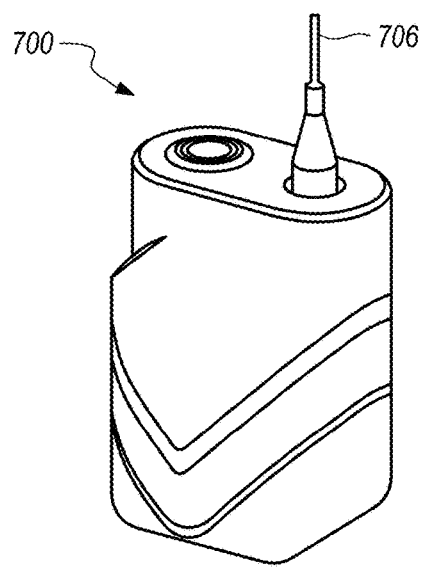
Figure 35C:
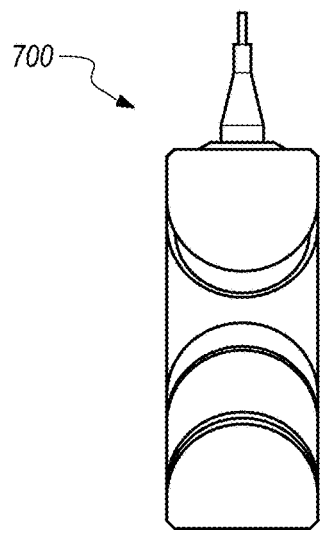
Figure 35D:
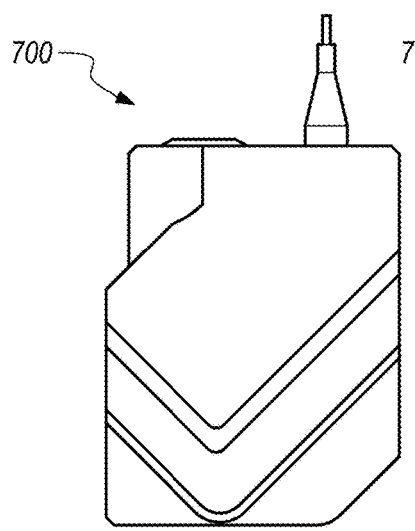
Figure 35E:
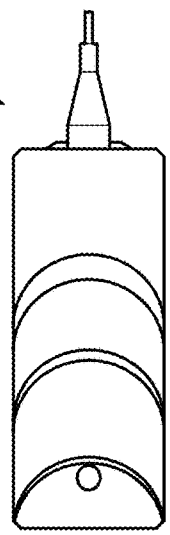
Figure 35F:
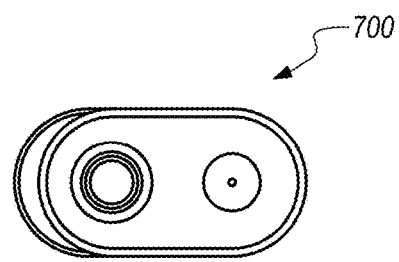

Referring to FIG. 35*a*-35*f,* shown is power device 700 for a fiber optic had piece for use in conjunction with the substrates and methods of the present invention. FIG. 35*a* shows the components of pocket power device 700, the pocket power device 700 further comprised of a base 701, a battery mount 702, a rechargeable battery 703, a handle for a fiber optic laser 704, and a top 705. FIG. 35*b*-35*f* show various views of the pocket power device 700. The handle 704 is a self-contained unit having an attached fiber optic line 706 upon which a fiber optic laser head (not shown) is connected. Further, a diode laser module is housed in pocket power device 700.

Figure 36A:
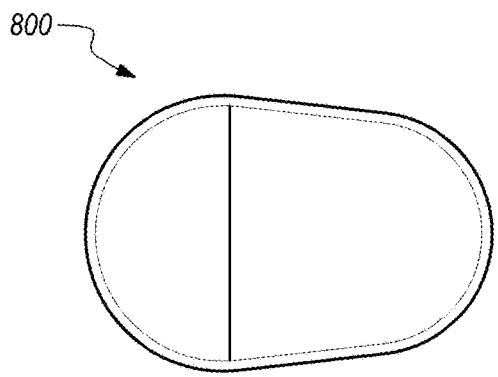
FIG. 36*a*-36*f* shows various views of a portable RF transmitter of the present invention. (a) shows a top view. (b) shows a front view. (c) shows a bottom view. (d) shows a left side view. (e) shows a left front perspective view. (f) shows a right front perspective view.
Figure 36B:
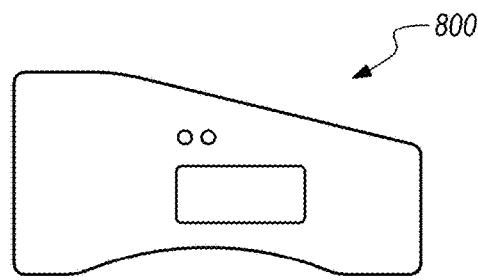
Figure 36C:
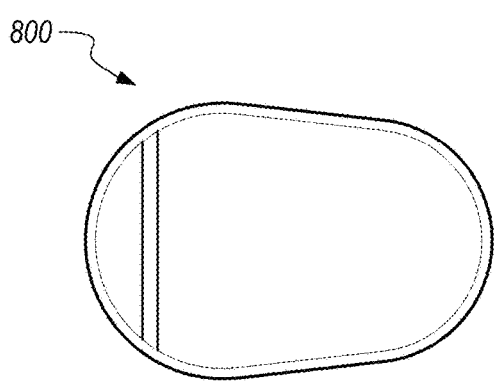
Figure 36D:
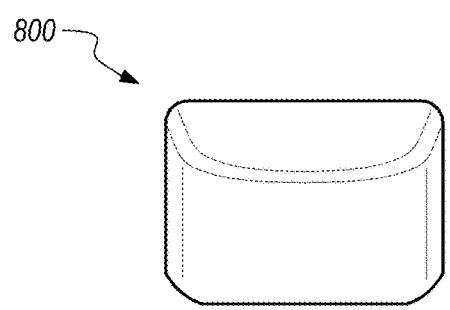
Figure 36E:
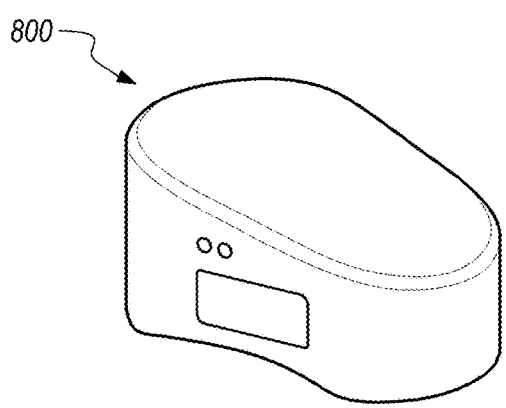
Figure 36F:
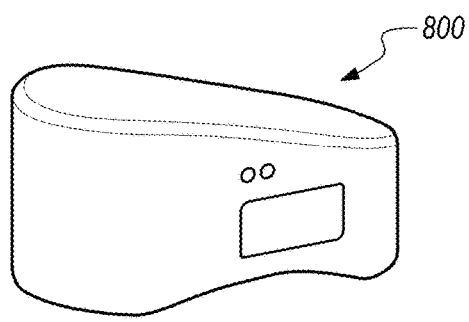

Referring to FIG. 36*a*-36*f,* shown is a portable RF transmitter 800 for use in conjunction with the substrates and methods of the present invention. FIGS. 36*e* and 36*f* show side perspective views of RF transmitter 800. FIG. 36*a* shows a top view; FIG. 36*b* shows front view; FIG. 36*c* shows a bottom view; and FIG. 36*d* shows a left side view. Optionally, the RF transmitter 800 may be used in the absence of substrates.

Examples

I. Analysis of Tooth #15 at 12 Unique Loci

A patient's pocket depths at tooth 15 were measured at 12 separate loci. The root of the tooth was then scaled and planed to remove calculus build up on the root surface. After scaling and planning, bleeding occurs in the sulcus. The sulcus was allowed to air dry and immediately thereafter the conditioner is applied to the sulcus and left for 30 seconds before being rinsed with saline. The tooth was next scaled and planed again to renew blood flow. With blood pooling in the sulcus, the 45° laser tip was placed into the sulcus. The laser light used has a wavelength in the visible portion of the electromagnetic spectrum, between 400 nm-700 nm wavelength. The laser was emitted continuously with only intermittent stops for tissue temperature control. The laser was allowed to penetrate the entire sulcus by moving the tip vertically and horizontally throughout the sulcus for 30 second. The laser tip was cut to 45° in the opposite angle for the second pass into the sulcus and 90° for the third pass to allow the laser bean to penetrate the existing periodontium to decontaminate and biostimulate the sulcular contents.

In the meantime, the first substrate and the second substrate were mixed in a glass dish. Some of the patient's blood that has been treated with the laser light in the sulcus was also mixed in the glass dish. This mixture is then placed immediately into the sulcus upon mixture. Enough of the mixture was placed into the sulcus to fill the sulcus while ensuring the mixture stayed 3 mm below the top of the gingival margin and remained immersed in blood. The patient's mouth was kept open for 5 minutes to ensure the newly formed blood clot containing the substrate mixture remained intact.

Figure 11:
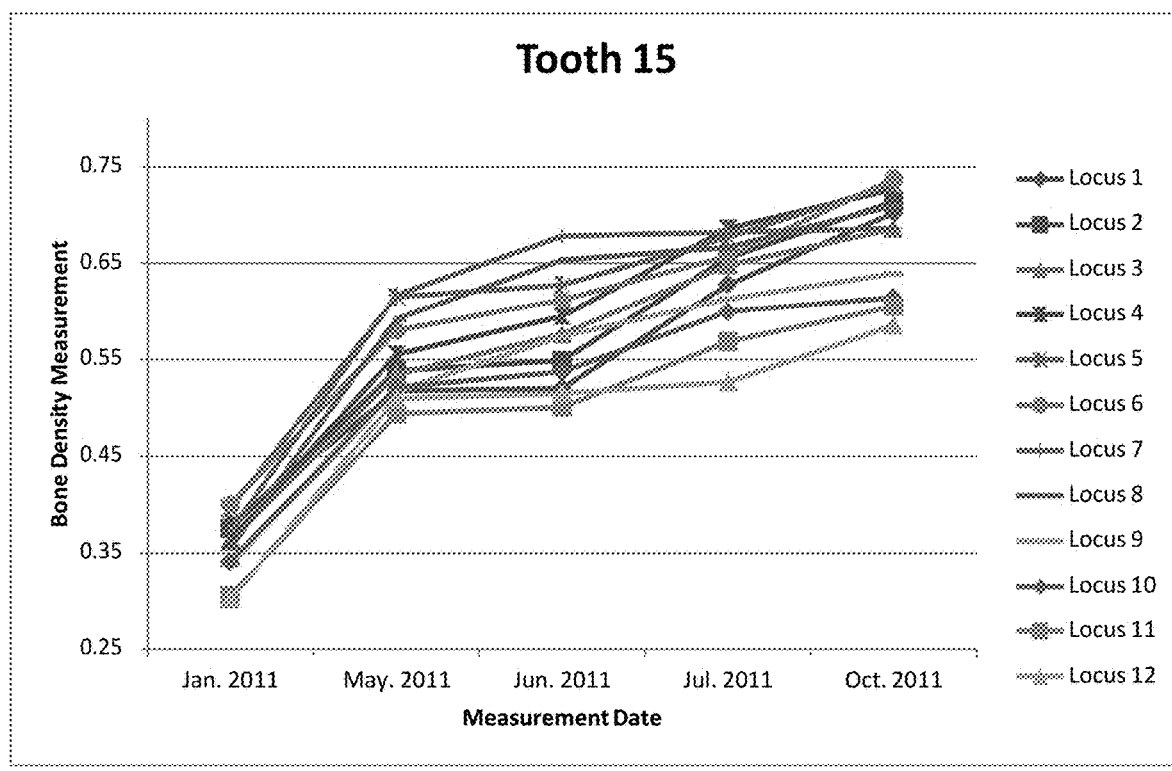
FIG. 11 shows bone density measurements for tooth 15 of a patient at 12 loci on the tooth following treatment with a diode laser and a substrate over time.

Treatment was repeated on tooth 15 on four subsequent occasions, at which time the pocket depths at each loci were measured prior to treatment. Measurements are shown in FIG. 11. The data show an increase in calcium density at the specific loci.

II. Analysis of Tooth #12 at 17 Unique Loci

Figure 12:
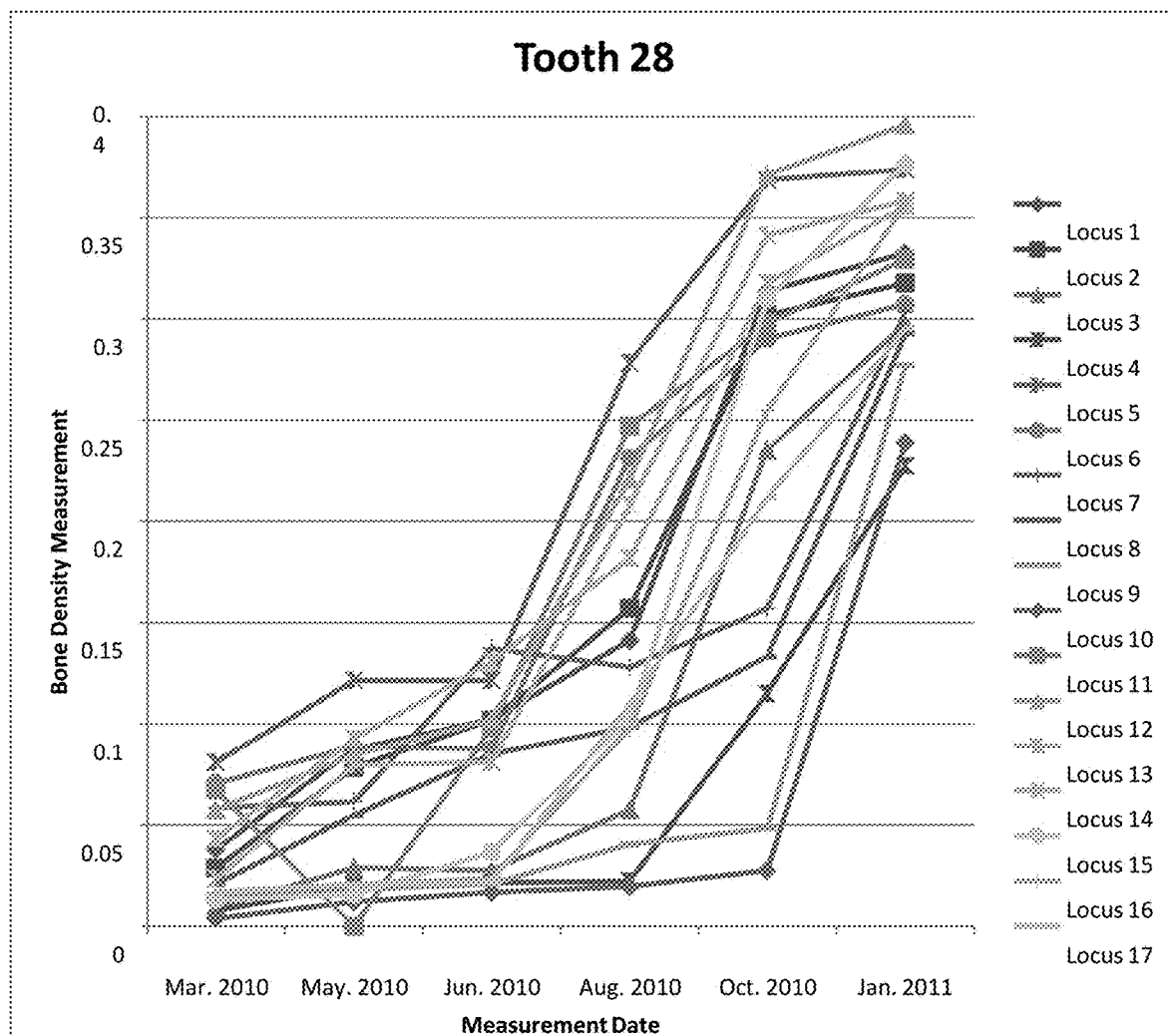
FIG. 12 shows bone density measurements for tooth 28 of a patient at 17 loci on the tooth following treatment with a diode laser and a substrate over time.

A patient's pocket depths at tooth 28 were measured at 17 separate loci. The treatment disclosed herein was performed on five subsequent occasions, at which time the pocket depths at each loci were measured prior to treatment. Measurements are shown in FIG. 12. The data show an increase in calcium density across all loci.

III. Analysis of Tooth #2, #3 and #15 at 3 Unique Loci Per Tooth

Figure 13:
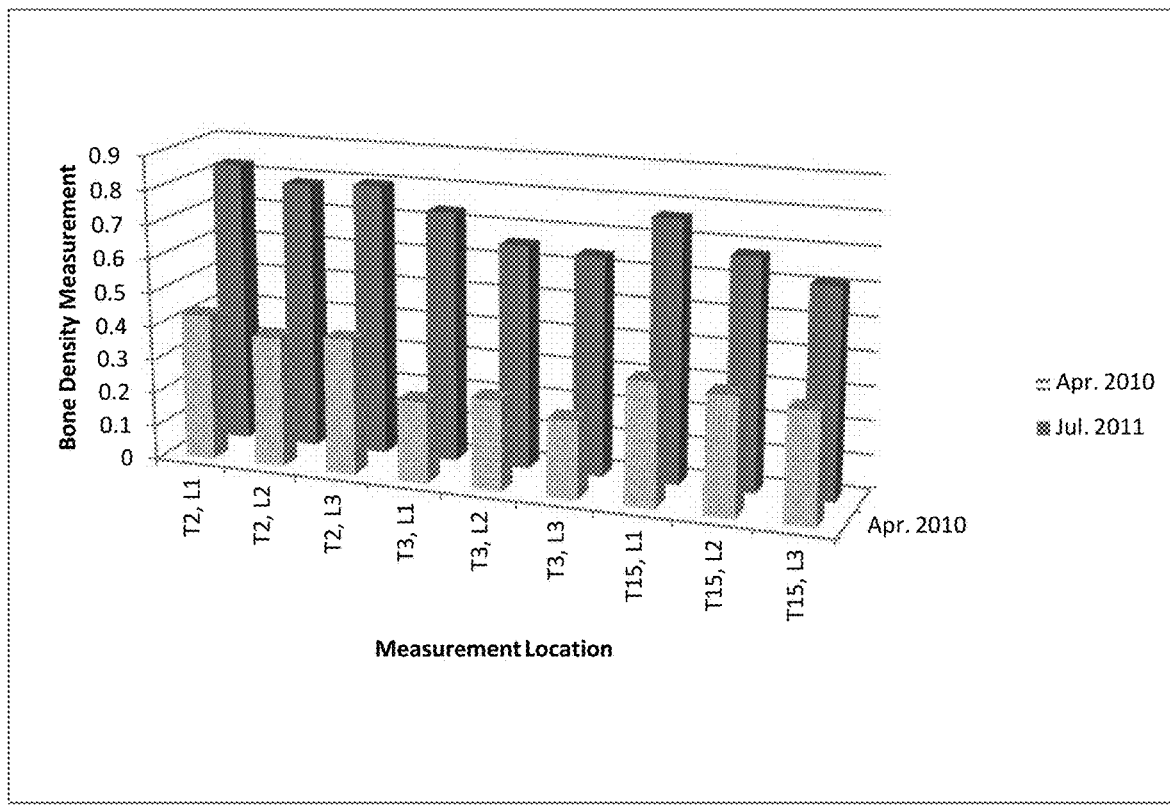
FIG. 13 shows bone density measurements for tooth 2, tooth 3 and tooth 15 of a patient at 3 loci per tooth following treatment with a diode laser and a substrate over time.
Figure 14A:
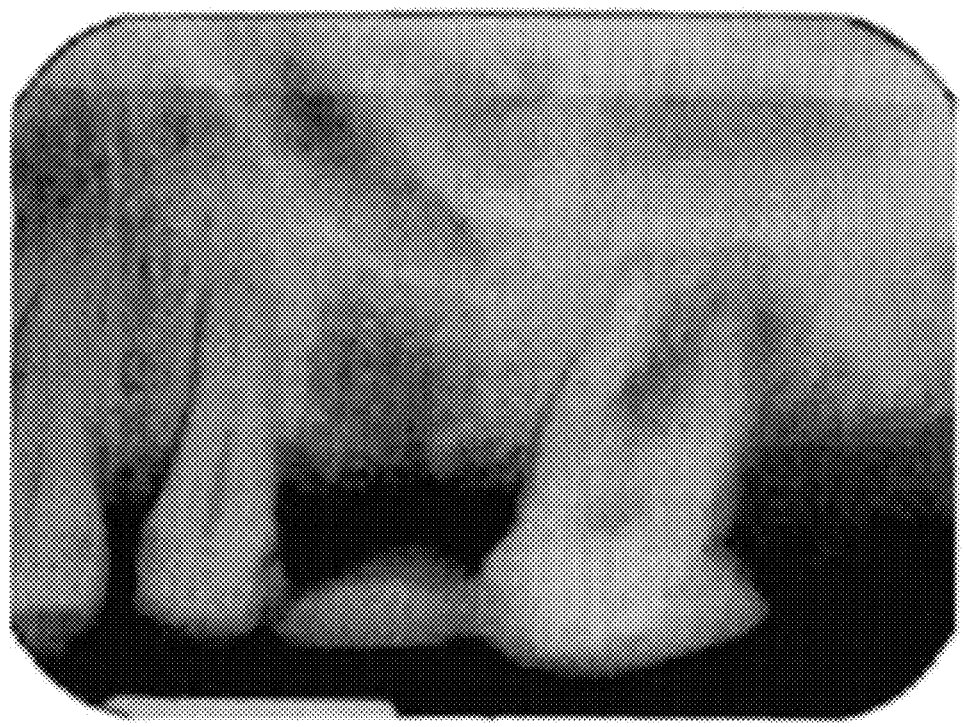
FIGS. 14a and 14b show X-rays of tooth 15 of a patient from which measurements shown in FIG. 11 were collected. (a) shows tooth 15 before treatment. (b) shows tooth 15 at the October 2011 measurement following three treatments.
Figure 14B:
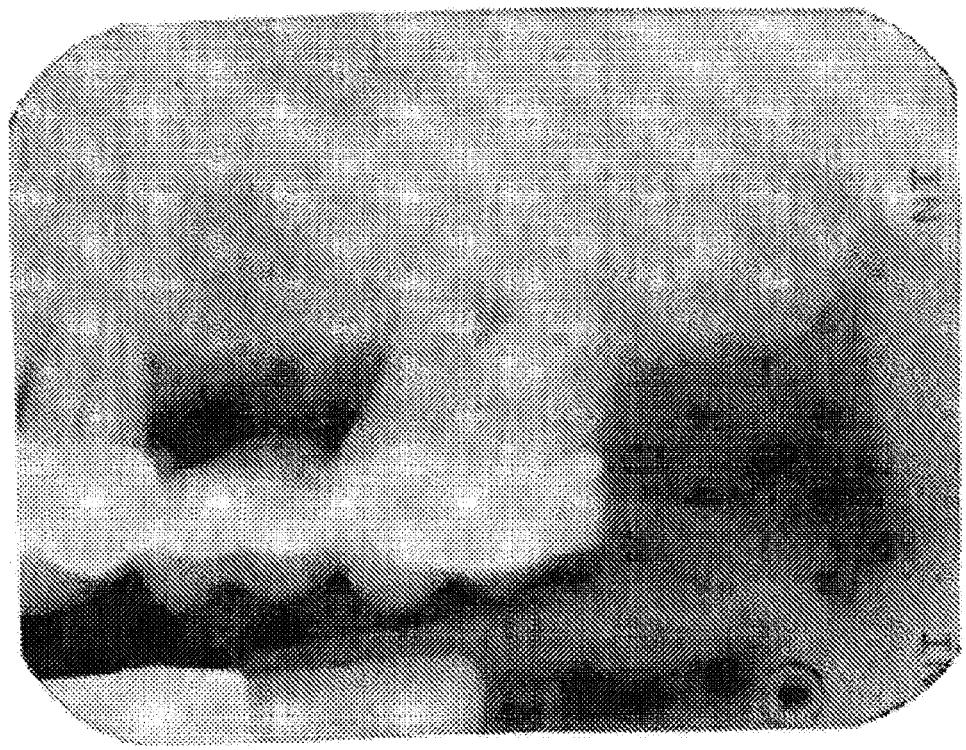
Figure 15A:
FIGS. 15a and 15b show X-rays of tooth 28 of a patient from which measurements shown in FIG. 12 were collected. (a) shows tooth 28 before treatment. (b) shows tooth 28 at the January 2011 measurement following four treatments.
Figure 15B:
Figure 16A:
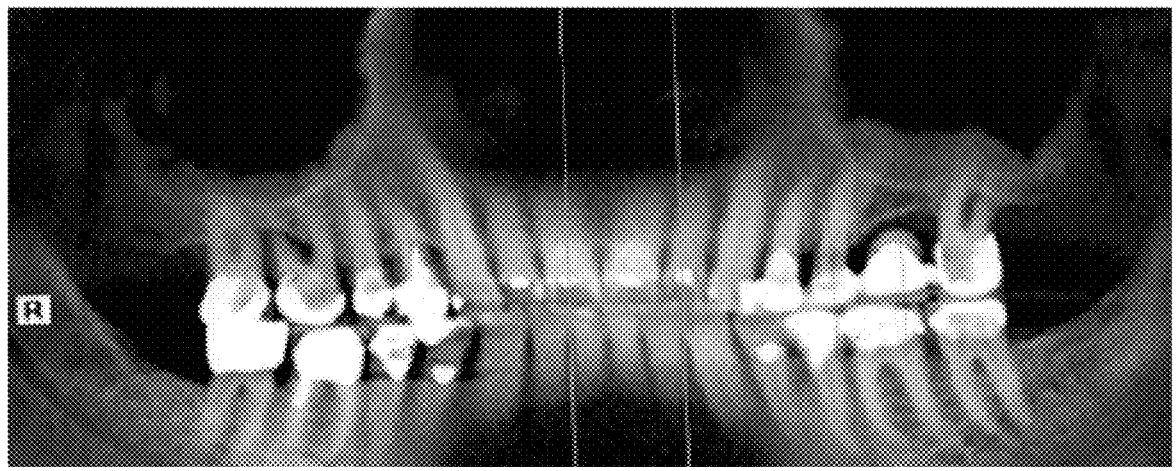
FIGS. 16a and 16b show a panoramic X-ray of tooth 2, tooth 3 and tooth 15 of a patient from which measurements shown in FIG. 13 were collected. (a) shows the teeth before treatment. (b) shows the teeth at the July 2011 measurement.
Figure 16B:
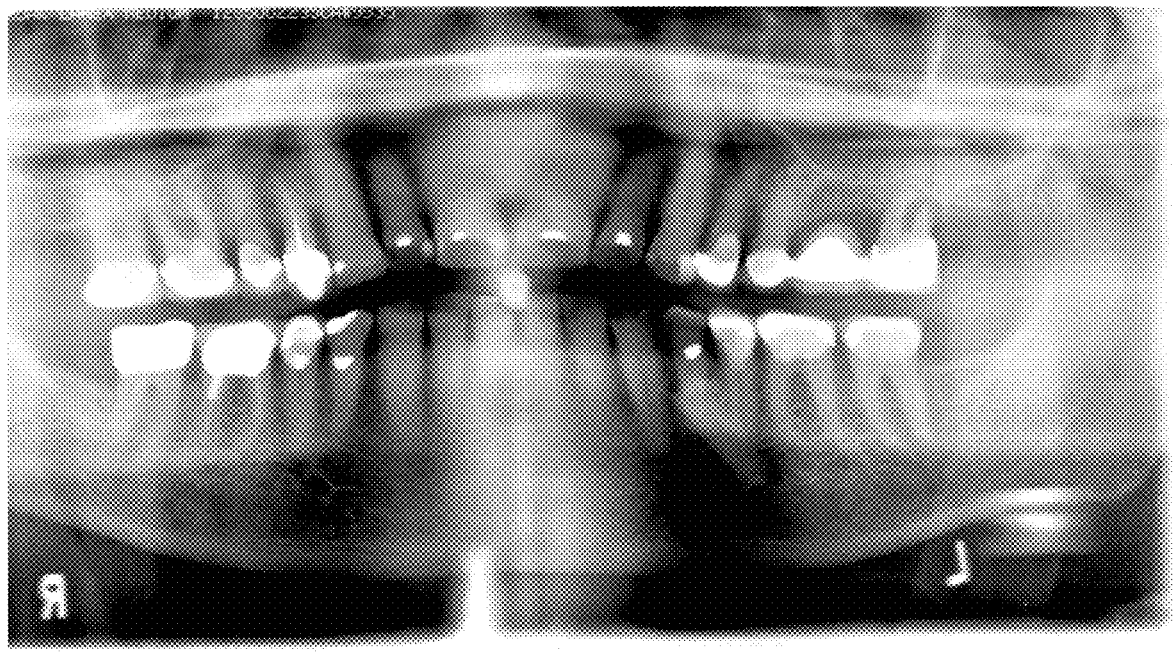

A patient's pocket depths at tooth 2, tooth 3 and tooth 15 were measured at three separate loci per tooth. The treatment disclosed herein was performed 3 months after the initial treatment, at which time the pocket depths at each loci were measured prior to treatment. Measurements are shown in FIG. 13. The data show a progression of bone generation.

IV. Analysis of Chin Profile

Figure 24:
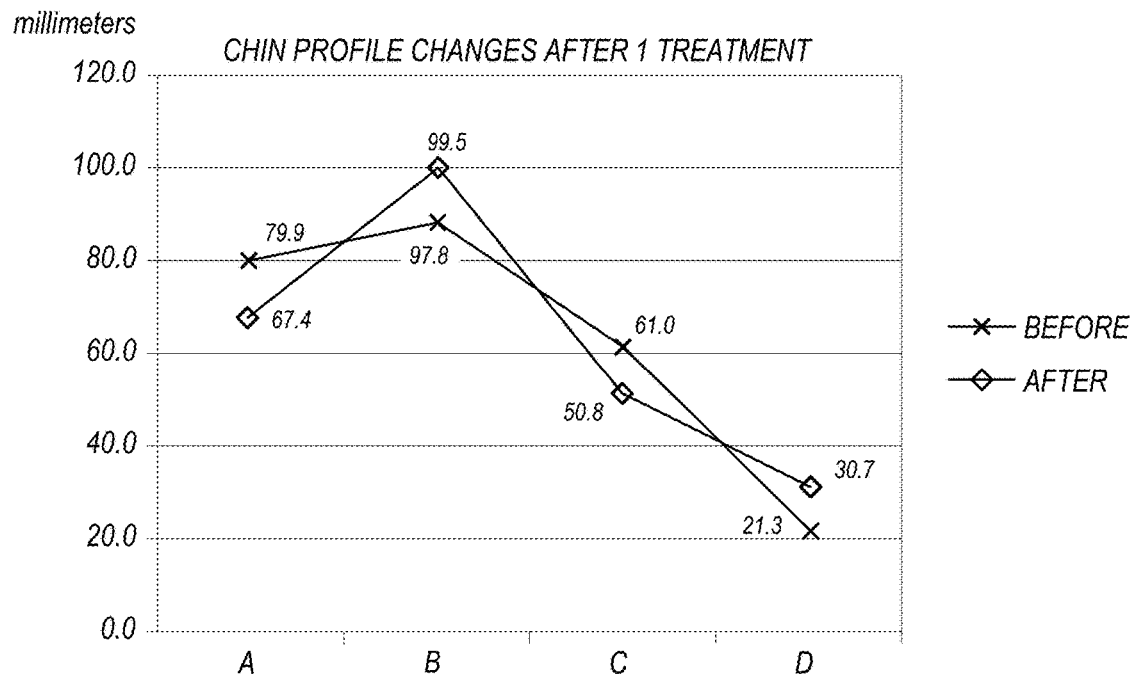
FIG. 24 shows chin profile measurements before and after treatment.

A patient's chin profile was measured. The treatment disclosed herein was performed once after the initial measurements were taken with measurements repeated following treatment. Measurements are shown in FIG. 24. The data show a general increase in chin profile following a single treatment.

V. Analysis of Toe Crease

Figure 25:
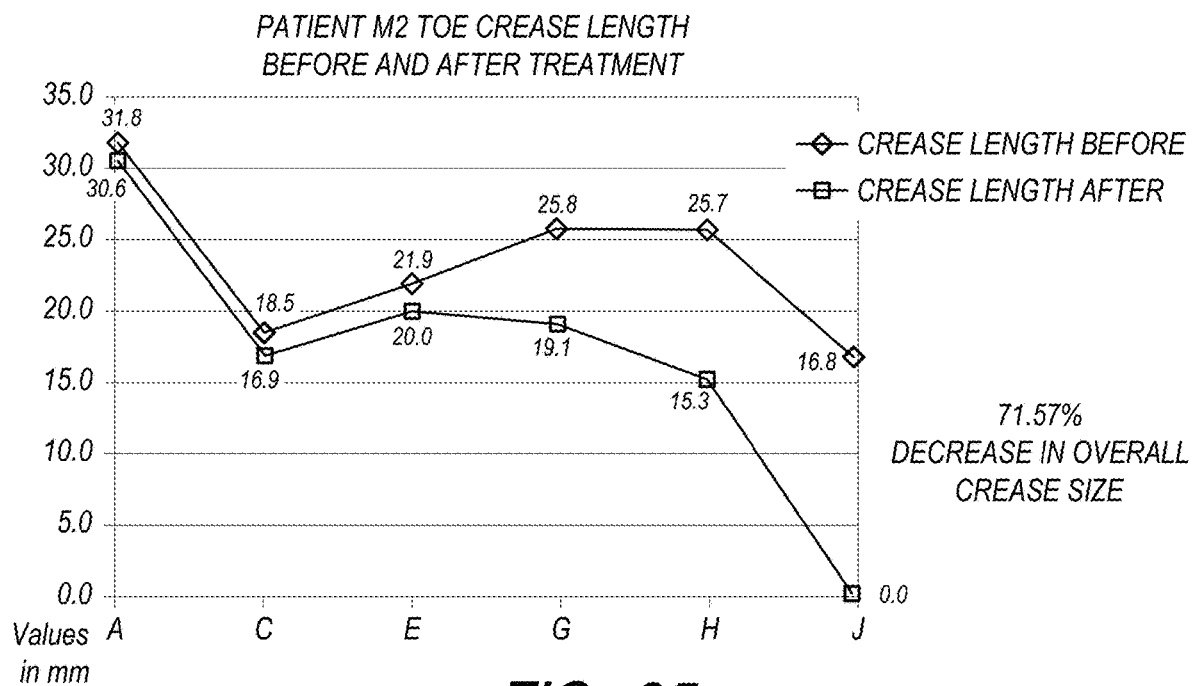
FIG. 25 shows toe crease length measurements before and after treatment.

A patient's toe crease length was measured. The treatment disclosed herein was performed after initial measurements were obtained with measurements repeated following treatment. Measurements are shown in FIG. 25. The data show a 71% overall decrease in crease size following treatment.

VI. Analysis of Gingival Wound Tissue

A patient's gingival wounds were measured from the line to the top of the gingiva. The treatment disclosed herein was performed and measurements were repeated following treatment. Images of gingival wounds are shown before and after treatment in FIGS. 26*a* and 26*b*. Measurements are shown in FIG. 26*c*. The data show a 50% or greater decrease in the wound following a single treatment.

VII. Analysis of Hand Crease

Figure 27:
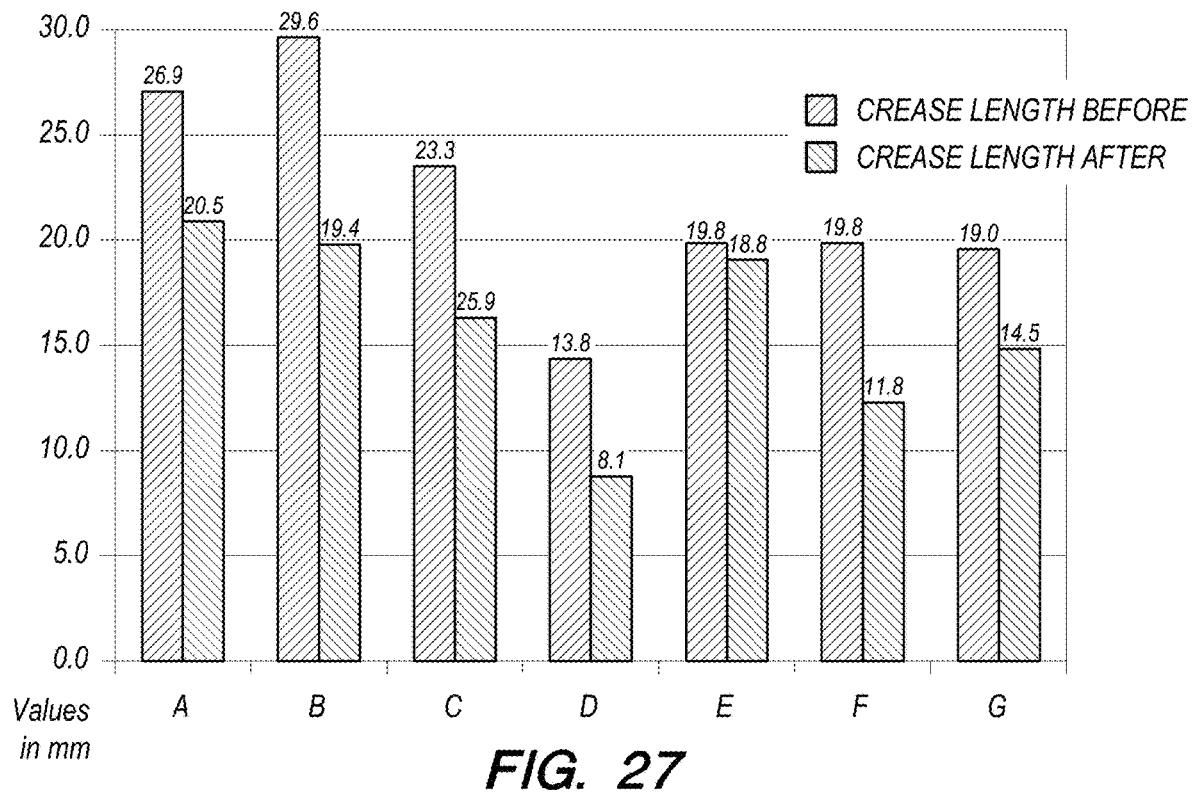
FIG. 27 shows hand crease length measurements before and after treatment.

A patient's hand crease length was measured. The treatment disclosed herein was performed after initial measurements were taken with measurements repeated following treatment. Measurements are shown in FIG. 27. The data show an overall decrease in crease length following treatment.

VIII. Analysis of New Skin Growth

Figure 28:
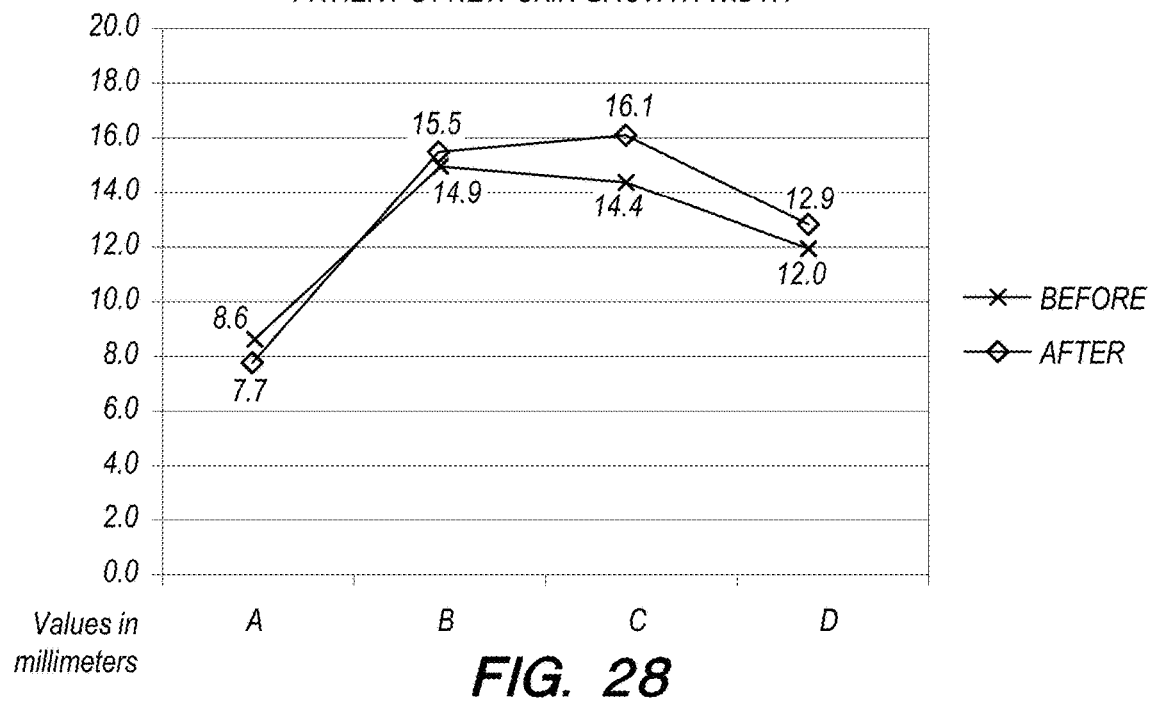
FIG. 28 shows wound new skin growth measurements before and after treatment.

A patient's skin leg wound was measured. The treatment disclosed herein was performed after initial measurements were taken with measurements repeated following treatment. Measurements are shown in FIG. 28. The data show an overall increase in new skin growth following treatment. In a preferred embodiment, chronic wounds on limbs may be treated using a three-sided LED system wherein the treatment unit is placed around the limb on three sides and applies the LED energy to a larger surface area. The LED system uses an energy source less than 500 mW per LED unit of light.

IX. Analysis of Anal Scar Reduction

Figure 29:
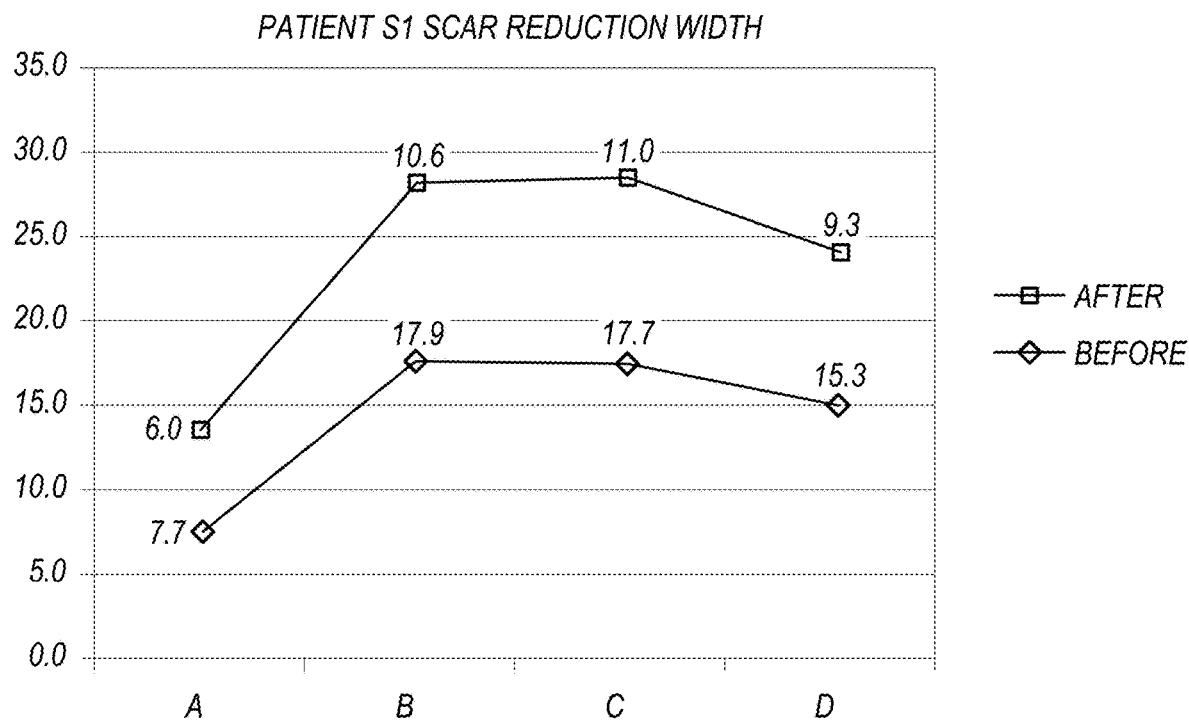
FIG. 29 shows (anal) scar width reduction measurements before and after treatment.
Figure 30:
FIG. 30 shows (anal) scar length reduction measurements before and after treatment.

A patient's anal scar tissue was measured. The treatment disclosed herein was performed after initial measurements were taken with measurements repeated following treatment. Measurements are shown in FIG. 29 and FIG. 30. The data show a reduction in both length and width of scar tissue following treatment.

X. Analysis of Tongue Strength

Figure 31:
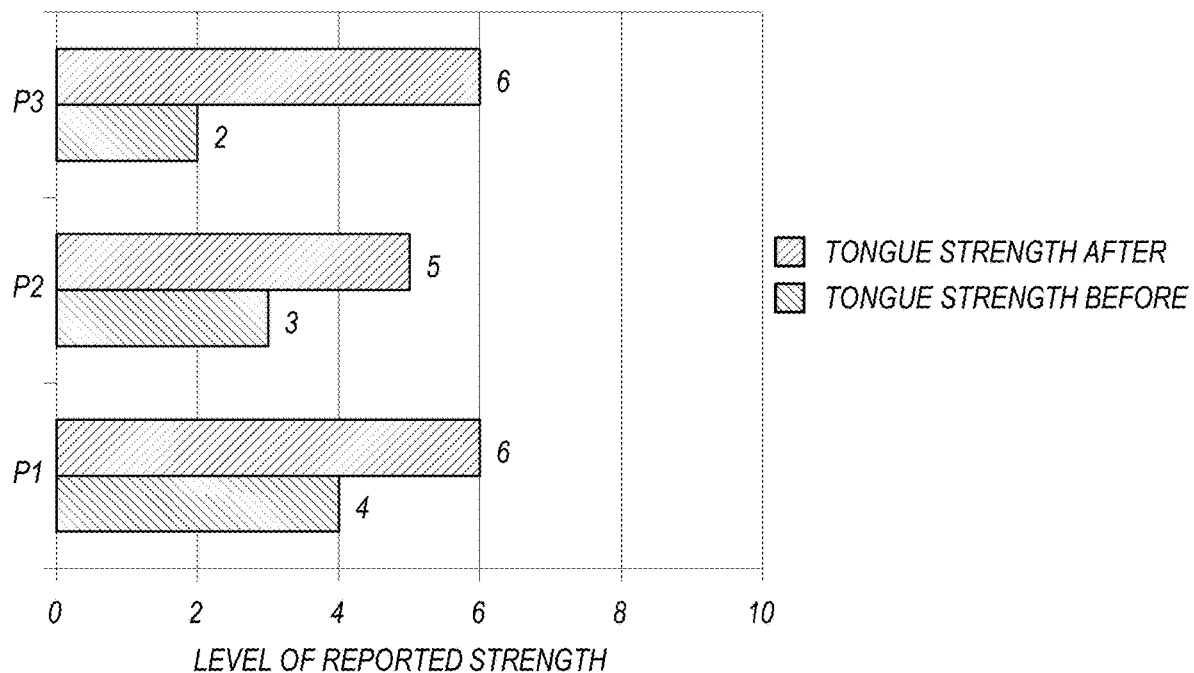
FIG. 31 shows swallowing strength measurements before and after treatment.

Tongue strength and swallowing was assessed for three patients. The treatment disclosed herein was performed after initial assessments were made and tongue strength and swallowing were reevaluated following treatment. Measurements are shown in FIG. 31. The data show each patient experiencing an increase in tongue strength following treatment.

XI. Analysis of Breast Firmness

Figure 32:
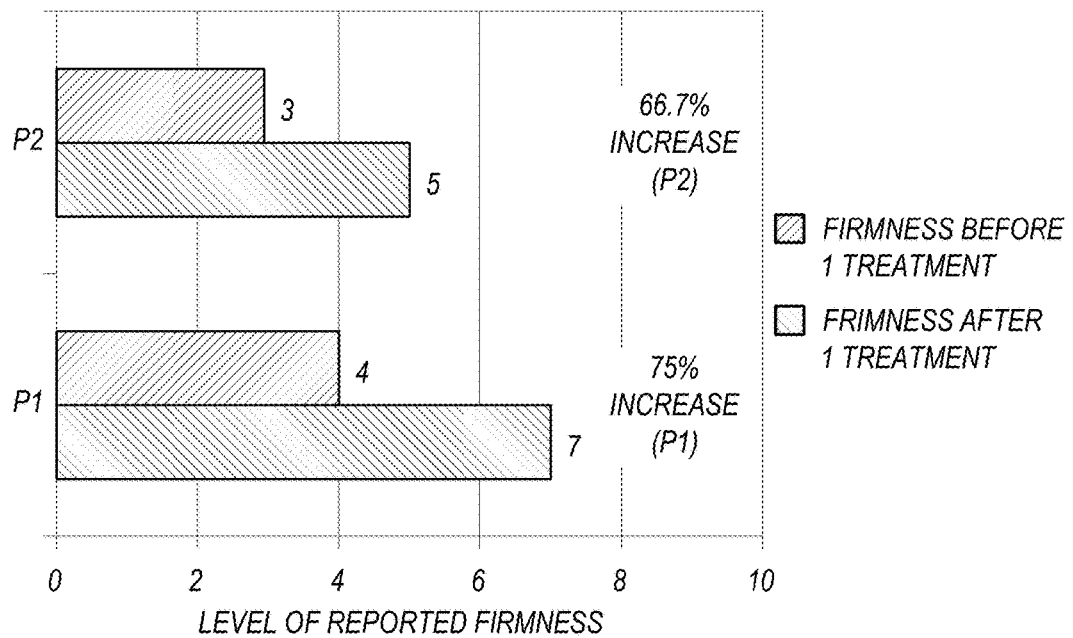
FIG. 32 shows breast firmness measurements before and after treatment.

Breast firmness was recorded for two patients. The treatment disclosed herein was performed after initial assessments were made and breast firmness was reevaluated following treatment. Comparative firmness is shown in FIG. 32. The data show the patients experiencing an increase in firmness of 75% and 66.7% following treatment, respectively.

XII. Analysis of Epithelial Wound Regeneration

Figure 37:
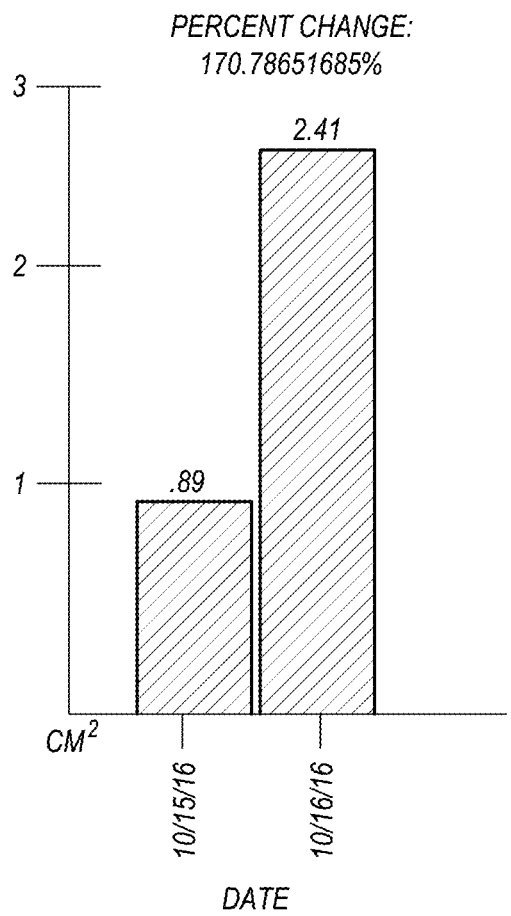
FIG. 37 shows epithelial wound regeneration before and after treatment.

The epithelial wound regeneration of a patient was assessed. The treatment disclosed herein was performed after initial wound measurement and wound size was remeasured following treatment. Comparative measurements are shown in FIG. 37. Epithelial regeneration was found to have increased in area by 170% one day following treatment.

XIII. Analysis of Calcaneal Tendon Wound Regeneration

Figure 38:
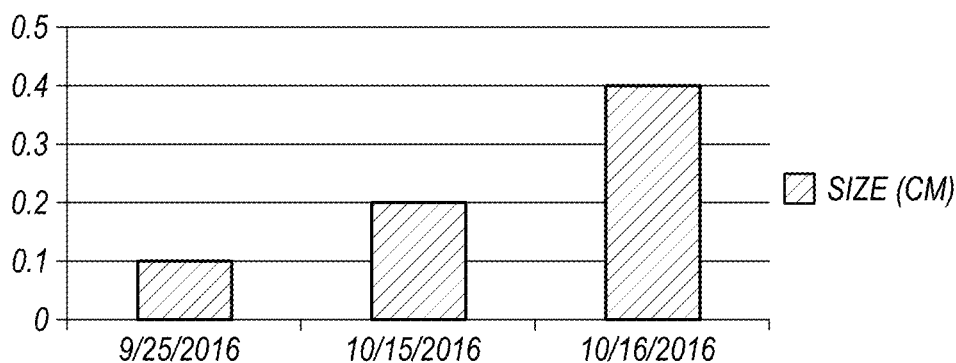
FIG. 38 shows cancaeal tendon wound regeneration before and after treatment.

The calcaneal tendon wound regeneration of a patient was assessed. The treatment disclosed herein was performed after initial wound measurement and wound size was remeasured following treatment. Comparative measurements are shown in FIG. 38. Tendon shelf size increased four times from the initial measurement to the third and final measurement.

XIII. Analysis of Ankle Epithelial Wound Regeneration

Figure 39:
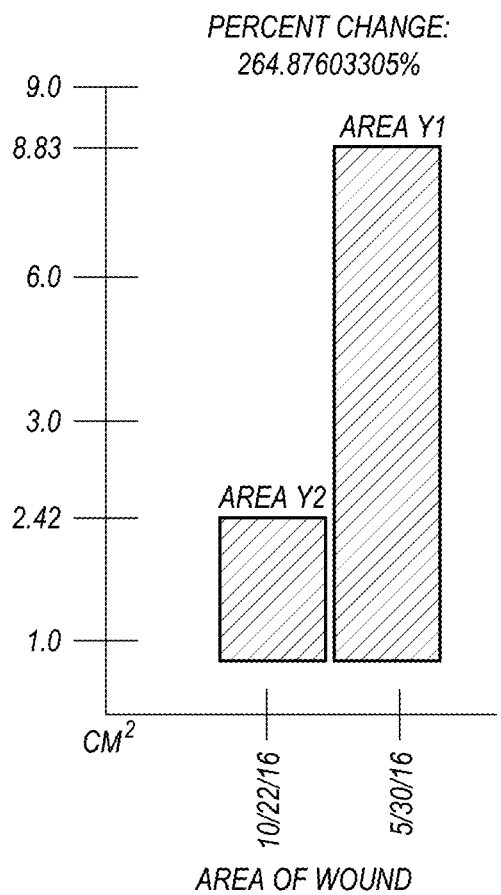
FIG. 39 shows ankle epithelial wound regeneration before and after treatment.

The ankle epithelial wound regeneration of a patient was assessed. The treatment disclosed herein was performed after initial wound measurement and wound size was remeasured following treatment. Comparative measurements for two treatment areas are shown in FIG. 39. Epithelial regeneration was found to have increased in area by 264% five months following treatment.

XIV. Analysis of Ankle Wound Size Reduction

The ankle epithelial wound size reduction of a patient was assessed. The treatment disclosed herein was performed after initial wound measurement and wound size was remeasured following treatment. Comparative measurements for two treatment areas are shown in FIG. 40. Epithelial wound size was found to have decreased in area by 72% five months following treatment.

XV. Analysis of Oral Cavity Wound Regeneration

Figure 41:
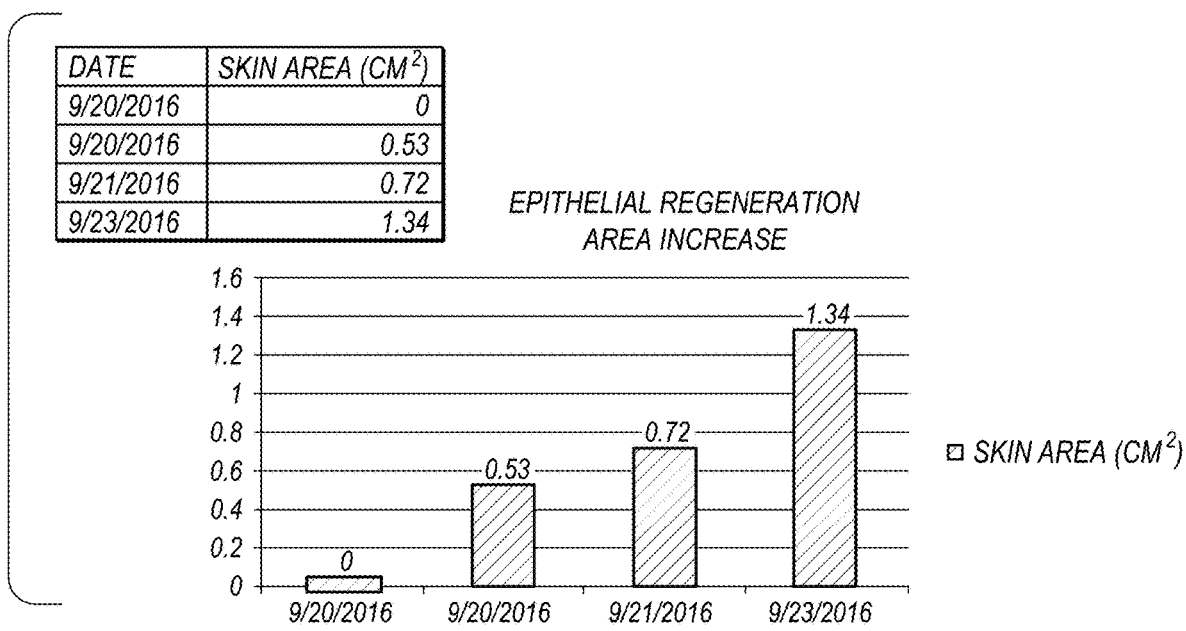
FIG. 41 shows oral cavity wound regeneration before and after treatment.

The oral cavity epithelial wound regeneration of a patient was assessed. The treatment disclosed herein was performed after initial wound measurement and wound size was remeasured following treatment. Comparative measurements are shown in FIG. 41. Epithelial regeneration size increased by 1.34 $cm^2$ from the initial measurement to the fourth and final measurement.

XVI. Analysis of Vein Wound Regeneration

Figure 42A:
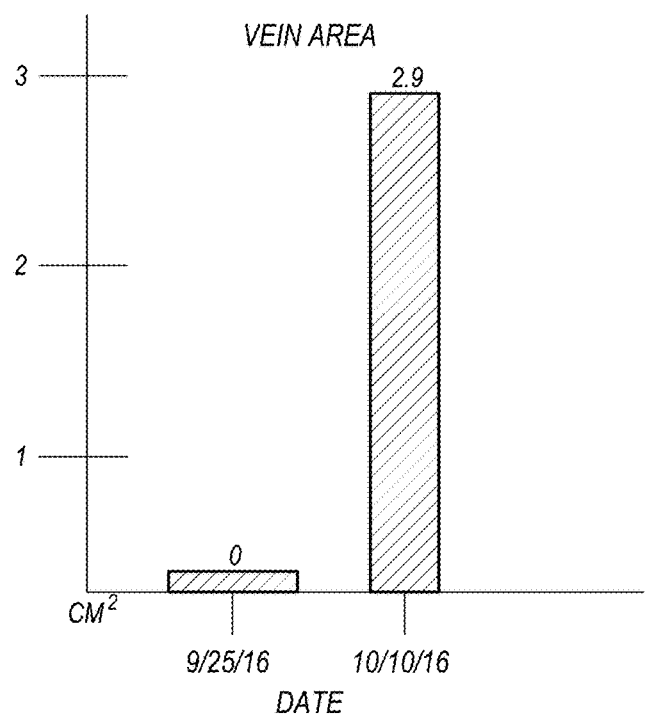
FIG. 42*a-b* shows (a) vein wound regeneration before and after treatment and (b) a flashlight style infrared laser.
Figure 42B:
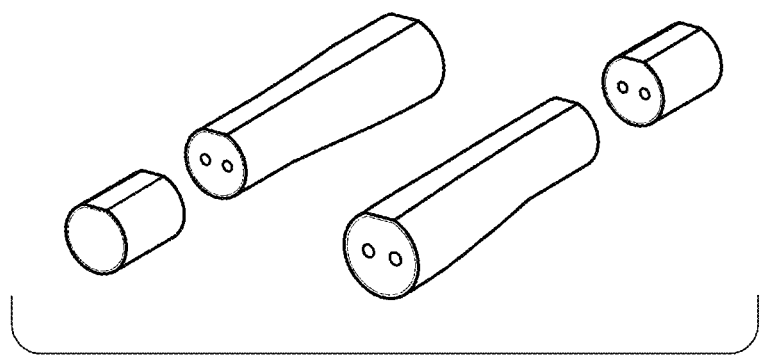

The vein wound regeneration of a patient was assessed. The treatment disclosed herein was performed after initial wound measurement and wound size was remeasured following treatment. Comparative measurements are shown in FIG. 42a. Epithelial regeneration size increased by 2.9 $cm^2$ from the initial measurement to final measurement. Treatment was conducted using a flashlight style infrared laser as shown in FIG. 42b wherein the LED beam is a concentrated flat line of light applied to the skin and veins. The flashlight style laser is a self-contained modular laser that allows for manipulation of skin around a wound during treatment. Alternatively, a LED panel may be used.

XVII. Analysis of Tissue Regeneration

Figure 43A:
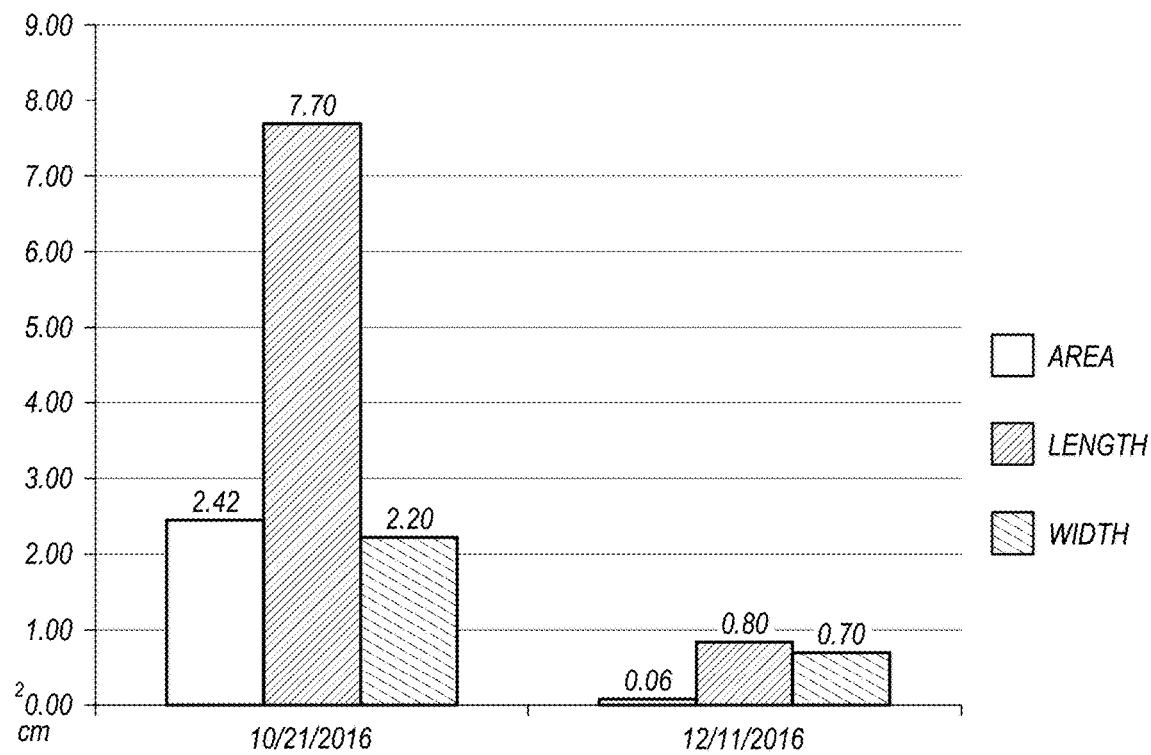
FIG. 43*a-b* shows increases in tissue regeneration in (a) epithelial tissue and (b) oral cavity wound.
Figure 43B:
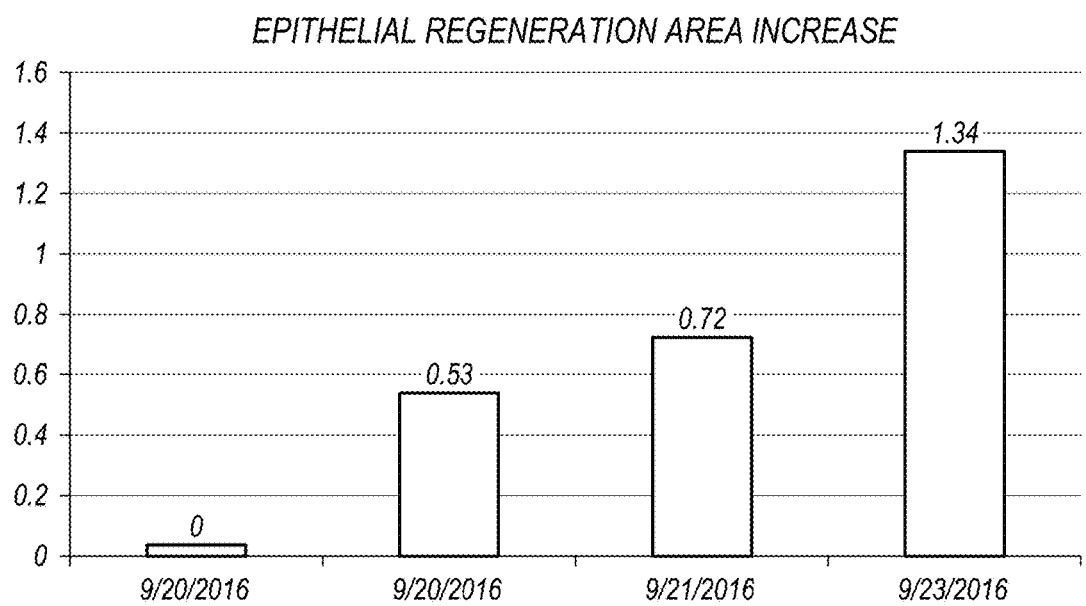

The wound regeneration of a patient was assessed and comparative measurements are shown at FIG. 43a. The wound was to epithelial tissue and the extent of the wound was first measured having an impacted length of 7.70 $cm^2$, a width of 2.20 $cm^2$ and an overall area of 2.42 $cm^2$. Six weeks later, the extent of the patient's wound was substantially reduced to a length of 0.8 $cm^2$, a width of 0.7 $cm^2$ and an overall area of 0.06 $cm^2$. Another patient was assessed with a wound in the oral cavity, with results detailed at FIG. 43b. As a measurement of new tissue regenerated, over a four day period, the patient exhibited a significant amount of increased skin area of regenerated tissue, starting with zero regeneration at day zero up to 1.34 $cm^2$ four days later.

One embodiment of the present invention provides a device for treating a wound according to the method described herein, the device emitting a laser a beam of light having a wavelength in the green wavelength range (520-570 nm), red wavelength range (620-750 nm), or yellow wavelength range (570-590 nm) having an alternative wattage of 0.001 W to 5 W, preferably 0.002 W to 4 W, more preferably 0.003 W to 3 W, and most preferably 0.005 W to 2 W. Optionally, the laser light utilizes the IR wavelength range (700 nm-1400 nm) at a laser power of 0.001 W to 5 W to treat wounds. Optionally, a LED light utilizes the IR wavelength range to treat wounds.

Another embodiment of the present invention provides a device for treating a wound according to the method described herein, the device emitting a RF beam up to 10 W or, preferably, 9 W comprised of a carrier wave frequency in the range of 0.1 MHz to 20 MHz and a non-sinusoidal waveform in the range of 0.5 to 40 KHz. In a preferred embodiment, the carrier wave frequency is in the range of 0.2 MHz to 10 MHz, preferably 0.3 MHz to 5 MHz. Optionally a 0.001 W to 10 W range RF energy, preferably a 0.001 W to 3 W range, is utilized in the hertz range of 40 Hz to 24 GHz. In a further alternative embodiment, the RF wave is more than one sine wave wherein the more than one demonstrates a harmonics pattern. Optionally, the non-sinusoidal waveform may be in the range of the above parameters as single or multiple waveforms in the presence or absence of a carrier wave.

Yet another embodiment of the present invention provides a device for treatment of a wound according to the method described herein, the device emitting a laser beam, a LED beam of light, a RF beam or a combination thereof.

Still another embodiment of the present invention provides a device for treatment of wounds in the oral cavity according to the method described herein, the device emitting a fiber optic laser beam. In a preferred embodiment, the fiber optic device may be used in conjunction with the laser, and/or RF device for treating general wounds and wounds of the oral cavity. Optionally, the device emits a LED light. Optionally more than one fiber can be in the handpiece and each fiber can be of a different wavelength and different average power.

While there have been shown and described and pointed out the fundamental novel features of the invention as applied to the preferred embodiments, it will be understood that the foregoing is considered as illustrative only of the principles of the invention and not intended to be exhaustive or to limit the invention to the precise forms disclosed.

Obvious modifications or variations are possible considering the above teachings. The embodiments discussed were chosen and described to provide the best illustration of the principles of the invention and its practical application to enable one of ordinary skill in the art to utilize the invention in various embodiments and with various modifications as are suited to the particular use contemplated All such modifications and variations are within the scope of the invention as determined by the appended claims when interpreted in accordance with the breadth to which they are entitled.

What is claimed is:

1. A device for treatment of wounds on or in an individual, the device having at least a first energy source and a second energy source configured to be used together with the first energy source, the first and second energy sources both configured for biostimulating soft and hard tissue, wherein:
the device has a handpiece and the first energy source is configured to generate an energy waveform having a wattage of less than 9 W for delivery to the soft and hard tissue;
the waveform has a frequency in a range of 0.5 Hz to less than 100 kHz; and
the second energy source comprises a light emitting diode (LED), or a diode laser, configured to generate light having a wavelength in a portion of an electromagnetic spectrum between 400 nm-1400 nm wavelength, with a power of 0.003 W to 3 W or 0.005 to 5 W average power per opening of the handpiece.

2. The device of claim 1, wherein the wavelength is selected from a group consisting of an infrared wavelength range (700-1400 nm), a green wavelength range (520-570 nm), a red wavelength range (620-750 nm), and a yellow wavelength range (570-590 nm).

3. The device of claim 1, wherein the energy waveform is more than one wave.

4. The device of claim 1, wherein the energy waveform is more than one square or sine wave.

5. The device of claim 1, wherein the second energy source is a laser.

6. The device of claim 1, further comprising a power source configured to power the device.

7. A device for treatment of wounds on or in an individual, the device having at least a first energy source and a second energy source configured to be used together with the first energy source, the first and second energy sources both configured for biostimulating soft and hard tissue, wherein the device has a handpiece and the first energy source is a light emitting diode (LED) or a diode laser, the LED or the laser configured to generate light having a wavelength in an electromagnetic spectrum between 400 nm -1400 nm for delivery to the soft and hard tissue, with a power of 0.003 W to 3 W or 0.005 to 5 W average power per opening of the handpiece;
wherein the light having the wavelength between 400 nm-1400 nm and energy from the second energy source are configured to cause tissue regeneration in a wound when delivered to the wound through the handpiece; and
wherein the LED or the diode laser is configured to generate the light having the wavelength between 400 nm-1400 nm, with the power of 0.003 W to 3 W or 0.005 to 4 W average power per opening of the handpiece with an energy waveform from the second energy source having a wattage of less than 4 W and a frequency in a range of 0.5 Hz to less than 100 KHz.

8. A device for treatment of wounds on or in an individual, the device having at least a first energy source configured for biostimulating soft and hard tissue, wherein the device has a handpiece and the first energy source is a light emitting diode (LED) configured to emit light onto the soft and hard tissue, the light having a wavelength in an electromagnetic spectrum between 400 nm -1400 nm, with a power of 0.003 W to 3 W or 0.005 to 5 W average power per opening of the handpiece;
wherein the light having the wavelength between 400 nm-1400 nm is configured to cause tissue regeneration in a wound when delivered to the wound through the handpiece together with an energy waveform having a wattage of less than 9 W and a frequency in a range of 0.5 Hz to less than 100 KHz.

9. A device for treatment of a wound on or in an individual, the device comprising first and second energy sources both configured for biostimulating soft and hard tissue, and a handpiece,
the first energy source configured to generate an energy waveform having a wattage of less than 4 W for delivery to the soft and hard tissue, wherein the waveform has a frequency in a range of 0.5 Hz to less than 100 kHz;
the second energy source configured to be used together with the first energy source, the second energy source comprising a light emitting diode or a diode laser configured to generate light having a wavelength in a portion of an electromagnetic spectrum between 400 nm-1400 nm for delivery to the soft and hard tissue; and
wherein the energy waveform having the wattage of less than 4 W and the light having the wavelength between 400 nm-1400 nm are configured to cause tissue regeneration in the wound when delivered to the wound through the handpiece.

\* \* \* \* \*